(12) United States Patent
Seki et al.

(10) Patent No.: US 7,439,368 B2
(45) Date of Patent: Oct. 21, 2008

(54) PROCESS FOR PRODUCING 3-ACYLAMINOBENZOFURAN-2-CARBOXYLIC ACID DERIVATIVE

(75) Inventors: Masahiko Seki, Nagaokakyo (JP); Shin-ichi Yoshida, Amagasaki (JP); Nobuhiro Yagi, Nara-ken (JP); Masanori Hatsuda, Otsu (JP); Mayumi Kimura, Yokohama (JP); Kazuhiko Kondo, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 87 days.

(21) Appl. No.: 10/561,180

(22) PCT Filed: Jun. 29, 2004

(86) PCT No.: PCT/JP2004/009488

§ 371 (c)(1),
(2), (4) Date: Dec. 16, 2005

(87) PCT Pub. No.: WO2005/000839

PCT Pub. Date: Jan. 6, 2005

(65) Prior Publication Data

US 2006/0173188 A1    Aug. 3, 2006

(30) Foreign Application Priority Data

Jun. 30, 2003  (JP) .............................. 2003-186370
Feb. 6, 2004   (JP) .............................. 2004-030794

(51) Int. Cl.
C07D 405/14   (2006.01)
C07D 405/12   (2006.01)

(52) U.S. Cl. .................................. 546/284.1; 549/467
(58) Field of Classification Search .............. 546/284.1; 549/467
See application file for complete search history.

(56) References Cited

FOREIGN PATENT DOCUMENTS

| EP | 1489078 A1 | 12/2004 |
|---|---|---|
| JP | 57-122062 A | 7/1982 |
| JP | 2001-039938 A | 2/2001 |
| WO | WO-99/14191 A1 | 3/1999 |
| WO | WO-02/085838 A1 | 10/2002 |

OTHER PUBLICATIONS

Djakovitch, L et al., Journal of Organometallic Chemistry, 1999, vol. 592, No. 2, pp. 225 to 234, p. 226, Scheme 1.
Ingold, K.U. et al., Journal of the Chemical Society, Perkin Transactions 2: Physical Organic Chemistry, 1972-1999, (1986), No. 8, p. 1337-44.
Viti, G. et al., Journal of heterocyclic Chemistry, 1990, vol. 27, No. 5, p. 1369-75, p. 1369, Scheme 1.
Harrison, C.R. et al., Journal of Organic Chemistry, 1983, vol. 48, No. 21, p. 3721-8, p. 3727, left col. (b).
Cable, et al., "Synthesis of Carbon-14 Labelled NK-1 Receptor Antagonists GR203040 and GR205171", Journal of Labelled Compounds and Radiopharmaceuticals, vol. 43, pp. 49-45, XP-002480616, 2000.

*Primary Examiner*—Patricia L Morris
(74) *Attorney, Agent, or Firm*—Birch, Stewart, Kolasch & Birch, LLP

(57) ABSTRACT

The present invention provides a process of preparing a compound of the formula [I]:

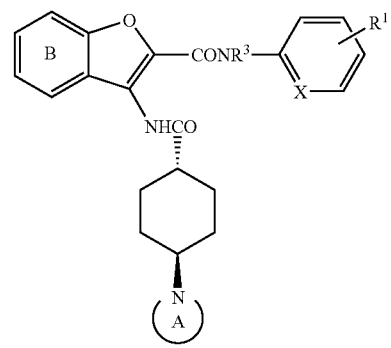

wherein X is a group of the formula: —N═ or —CH═; $R^1$ is a hydrogen atom, a halogen atom, a lower alkyl group, a lower alkoxy group, a cyano group or an amino group optionally substituted by a lower alkyl group; Ring A is a nitrogen-containing heterocyclic group; Ring B is an optionally substituted benzene ring or an optionally substituted pyridine ring; and $R^3$ is a hydrogen atom or a lower alkyl group, or a pharmaceutically acceptable salt thereof, which is useful as an inhibitor of activated blood coagulation factor X.

31 Claims, No Drawings

PROCESS FOR PRODUCING 3-ACYLAMINOBENZOFURAN-2-CARBOXYLIC ACID DERIVATIVE

TECHNICAL FIELD

The present invention relates to a process for preparing a benzofuran derivative or a pyridofuran derivative, or a pharmaceutically acceptable salt thereof, which is useful as a medicament, particularly as an inhibitor of activated blood coagulation factor X.

BACKGROUND ART

Benzofuran derivatives or pyridofuran derivatives of the formula [I]:

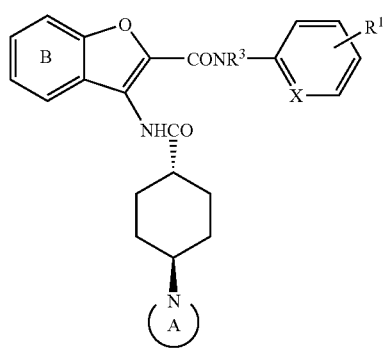

wherein X is a group of the formula: —N= or —CH=; $R^1$ is a hydrogen atom, a halogen atom, a lower alkyl group, a lower alkoxy group, a cyano group or an amino group optionally substituted by a lower alkyl group; Ring A is a nitrogen-containing heterocyclic group; Ring B is an optionally substituted benzene ring or an optionally substituted pyridine ring; and $R^3$ is a hydrogen atom or a lower alkyl group, or a pharmaceutically acceptable salt thereof, which is useful as a medicament, particularly as an inhibitor of activated blood coagulation factor X, and a process for preparing the same are disclosed in WO03/082847 and Japanese Patent Application No. 2003-84865 (JP-2004-250417, A).

However, the process disclosed in WO03/082847 and Japanese Patent Application No. 2003-84865 (JP-2004-250417, A) involves many steps, and, therefore, the development of an industrially advantageous manufacturing process involving fewer steps has been demanded.

DISCLOSURE OF INVENTION

The present invention provides an excellent process for efficiently preparing a novel benzofuran derivative or a pyridofuran derivative, or a pharmaceutically acceptable salt thereof, which is useful as an inhibitor of activated blood coagulation factor X.

The present inventors have intensively studied and found a process for preparing a benzofuran derivative or a pyridofuran derivative, or a pharmaceutically acceptable salt thereof, which process is industrially advantageous and involves fewer steps, and have accomplished the present invention.

That is, the present invention is as follows:

1. A process for preparing a compound of the formula [1]:

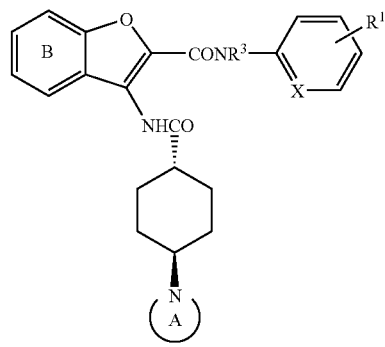

wherein X is a group of the formula: —N= or —CH=; $R^1$ is a hydrogen atom, a halogen atom, a lower alkyl group, a lower alkoxy group, a cyano group or an amino group optionally substituted by a lower alkyl group; Ring A is a nitrogen-containing heterocyclic group; Ring B is an optionally substituted benzene ring or an optionally substituted pyridine ring; and $R^3$ is a hydrogen atom or a lower alkyl group, or a pharmaceutically acceptable salt thereof, which comprises:

(A)

1)-a) reacting a compound of the formula [II]:

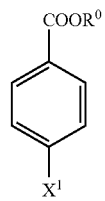

wherein $R^0$ is a hydrogen atom or a lower alkyl group and $X^1$ is a leaving group with a compound of the formula [III]:

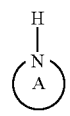

wherein Ring A is a nitrogen-containing heterocyclic group, or

1)-b) reacting a compound of the formula [IV]:

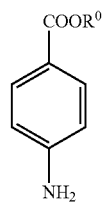

wherein the symbol is the same as defined above with a compound of the formula [V]:

wherein A' is a group derived from a nitrogen-containing heterocyclic group by removing a nitrogen atom, and $X^2$ and $X^3$ are leaving groups;

2) subjecting the resulting compound of the formula [VI]:

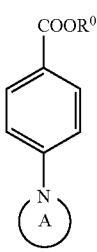

wherein the symbols are the same as defined above to catalytic reduction;

3) subjecting the resulting compound of the formula [VII]:

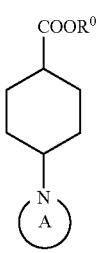

wherein the symbols are the same as defined above to lower-alkyl esterification when $COOR^0$ is a carboxyl group, followed by isomerization to give a trans-form compound of the formula [VIII]:

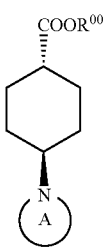

wherein $R^{00}$ is a hydrogen atom or a lower alkyl group and the other symbol is the same as defined above; and separately, (B)
1) cyanation of a compound of the formula [IX]:

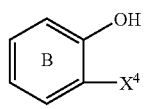

wherein Ring B is an optionally substituted benzene ring or an optionally substituted pyridine ring and $X^4$ is a leaving group, 2) reacting the resulting compound of the formula [X]:

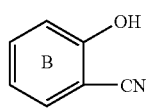

wherein the symbol is the same as defined above with a compound of the formula [XI]:

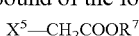

wherein $R^7$ is a hydrogen atom or an ester residue and $X^5$ is a leaving group, and reacting the resulting compound of the formula [XII]:

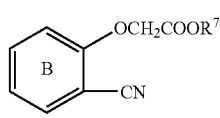

wherein the symbols are the same as defined above with a compound of the formula [XIII]:

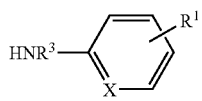

wherein $R^3$ is a hydrogen atom or a lower alkyl group, $R^1$ is a hydrogen atom, a halogen atom, a lower alkyl group, a lower alkoxy group, a cyano group or an amino group optionally substituted by a lower alkyl group and X is a formula: —N= or —CH=, after converting the group $R^7$ of the compound [XII] to a hydrogen atom, when $R^7$ is an ester residue, 3) cyclizing the resulting compound of the formula [XIV]:

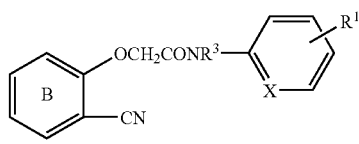

wherein the symbols are the same as defined above to give a compound of the formula [XV]:

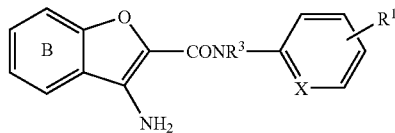

wherein the symbols are the same as defined above; and (C)

reacting a compound of the formula [XV] with a compound of the formula [VIII] or a reactive derivative thereof.

2. A process for preparing a compound of the formula [VI']:

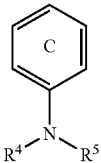

wherein Ring C is an optionally substituted aromatic ring and the formula: $NR^4R^5$ is an optionally substituted amino group or an optionally substituted nitrogen-containing heterocyclic group, which comprises reacting a compound of the formula [II']:

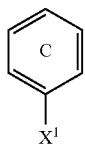

wherein $X^1$ is a leaving group and other symbol is the same as defined above with a compound of the formula [III']:

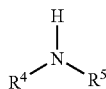

wherein the symbols are the same as defined above in the presence of a group VIII metal compound supported by a solid phase.

3. A process for preparing a compound of the formula [VI]:

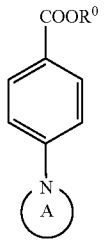

wherein $R^0$ is a hydrogen atom or a lower alkyl group and Ring A is a nitrogen-containing heterocyclic group, which comprises reacting a compound of the formula [IV]:

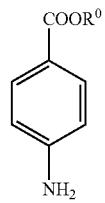

wherein the symbol is the same as defined above with a compound of the formula [V]:

wherein A' is a group derived from a nitrogen-containing heterocyclic group by removing a nitrogen atom, and $X^2$ and $X^3$ are leaving groups.

4. A process for preparing a compound of the formula [VII"]:

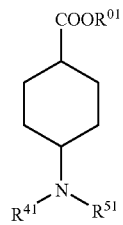

wherein $R^{01}$ is a hydrogen atom and the formula: $NR^{41}R^{51}$ is a substituted amino group or a substituted nitrogen-containing heterocyclic group, which comprises subjecting a compound of the formula [VI"]:

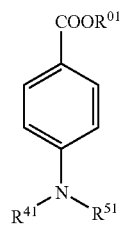

wherein the symbols are the same as defined above to catalytic reduction under low pressure and neutral to slightly basic conditions.

5. A process for preparing a trans-form compound of the formula [VIII"]:

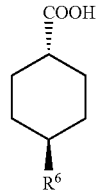

wherein R⁶ is a substituent, or a carboxylic acid derivative thereof, which comprises isomerizing a cis-form or a mixture of cis- and trans-forms of a carboxylic acid derivative of the formula [VII']:

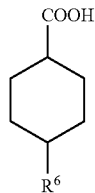

wherein the symbol is the same as defined above in the presence of an alkali metal alkoxide or an alkali metal amide.

6. A process for preparing a compound of the formula [X']:

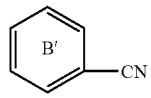

wherein Ring B' is an optionally substituted aromatic ring, which comprises cyanation of a compound of the formula [IX']:

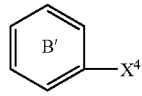

wherein X⁴ is a leaving group and other symbol is the same as defined above in the presence of a group VIII metal compound supported by a solid phase.

7. A process for preparing a compound of the formula [XIV]:

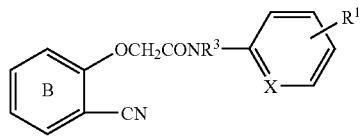

wherein Ring B is an optionally substituted benzene ring or an optionally substituted pyridine ring, R³ is a hydrogen atom or a lower alkyl group, R¹ is a hydrogen atom, a halogen atom, a lower alkyl group, a lower alkoxy group, a cyano group or an amino group optionally substituted by lower alkyl group and X is a formula: —N═ or —CH═ from a compound of the formula [XII']:

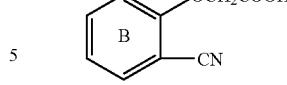

wherein the symbol is the same as defined above and a compound of the formula: [XIII]:

wherein the symbols are the same as defined above, which comprises adding a weak base to form a salt of compound [XII'], treating the salt with a halogenating agent to form an acid chloride, and reacting the acid chloride with the compound [XIII].

8. A process for preparing a compound of the formula [XV]:

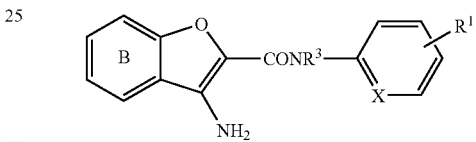

wherein Ring B is an optionally substituted benzene ring or an optionally substituted pyridine ring, R³ is a hydrogen atom or a lower alkyl group, R¹ is a hydrogen atom, a halogen atom, a lower alkyl group, a lower alkoxy group, a cyano group or an amino group optionally substituted by lower alkyl group and X is a formula: —N═ or —CH═, which comprises cyclizing a compound of the formula [XIV]:

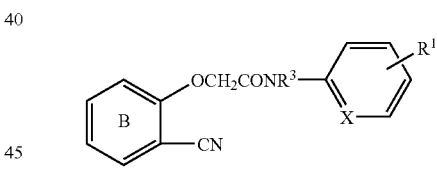

wherein the symbols are the same as defined above.

9. A process for preparing a compound of the formula [VII''']:

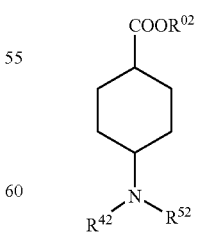

wherein $R^{02}$ is a lower alkyl group and the formula: $NR^{42}R^{52}$ is a substituted amino group or a substituted nitrogen-containing heterocyclic group, which comprises subjecting a compound of the formula [VI''']:

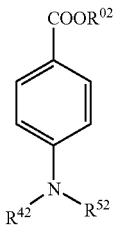

wherein the symbols are the same as defined above to catalytic reduction under low pressure.

10. A process for preparing a compound of the formula [VII''''']:

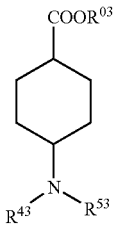

wherein $R^{03}$ is a lower alkyl group and the formula: $NR^{43}R^{53}$ is an unsubstituted amino group, which comprises subjecting a compound of the formula [VI''''']:

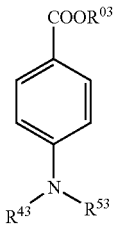

wherein the symbols are the same as defined above to catalytic reduction under low pressure and neutral to slightly basic conditions.

11. The process according to 2, which is carried out in the presence of a palladium-carbon catalyst, a ligand and a base under nitrogen.
12. The process according to 11, which is carried out in a mixed solvent comprising t-butyl alcohol.
13. The process according to 12, which is carried out at 0-200° C.
14. The process according to 4, which is carried out in the presence of a rhodium-carbon catalyst.
15. The process according to 5, which is carried out at 0-80° C.
16. The process according to 6, which is carried out in the presence of a palladium-carbon catalyst, zinc and a ligand.
17. The process according to 16, which is carried out at 0-200° C.
18. The process according to 8, which is carried out in the presence of a strong organic base.

Specific examples of objective compounds of the process of the present invention include those wherein Ring B is a benzene ring or a pyridine ring each being optionally substituted by a group(s) selected independently from a halogen atom, an optionally substituted lower alkyl group, a hydroxy group, an optionally substituted lower alkoxy group, an oxy group substituted by an optionally substituted saturated heterocyclic group, a substituted carbonyl group, an optionally substituted amino group, a nitro group, a cyano group, a 4,5-dihydroxazolyl group and a group of the formula: —C(NH$_2$)=N—OH; and the "nitrogen-containing heterocyclic group" for Ring A is an optionally substituted group of a formula selected from the formulas:

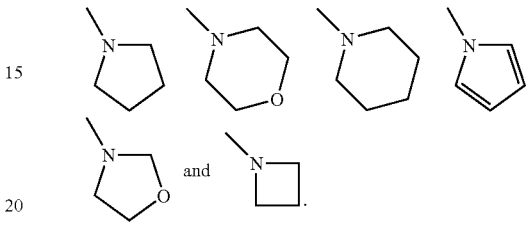

Above all, examples of preferred objective compounds include those wherein the "nitrogen-containing heterocyclic group" for Ring A is a group of a formula selected from the formulas:

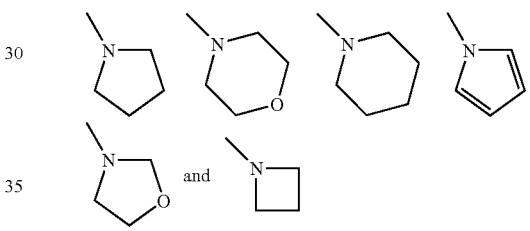

which is optionally substituted by an oxo group;
the "optionally substituted lower alkyl group" as a substituent for Ring B is a lower alkyl group optionally substituted by a group selected from the followings:
(1) a lower alkoxycarbonyl group,
(2) a carboxyl group,
(3) a carbamoyl group optionally substituted by a group selected from (a) a lower alkyl group, (b) a lower alkoxy-lower alkyl group, (c) a lower alkyl group substituted by a hydroxyl group, and (d) a lower alkoxy group,
(4) a carbonyl group substituted by a morpholinyl group,
(5) a piperidylcarbonyl group substituted by a hydroxy-lower alkyl group,
(6) a pyrrolidinylcarbonyl group substituted by a hydroxy-lower alkyl group,
(7) a carbonyl group substituted by a hydroxyl group-substituted piperidyl group, and
(8) a hydroxyl group;
the "optionally substituted lower alkoxy group" as a substituent for Ring B is a lower alkoxy group optionally substituted by a group selected from the followings:
(1) a carboxyl group,
(2) a lower alkoxycarbonyl group,
(3) a lower alkoxy group,
(4) a hydroxyl group,
(5) an aminooxy group optionally substituted by a lower alkoxycarbonyl group, (6) a lower alkoxy group substituted by a lower alkoxy group,
(7) a carbonyl group substituted by a morpholinyl group, a piperidyl group or a pyrrolidinyl group,
(8) a carbonyl group substituted by a hydroxypiperidyl group,
(9) a piperidylcarbonyl group substituted by a hydroxy-lower alkyl group,
(10) a pyrrolidinylcarbonyl group substituted by a hydroxy-lower alkyl group,
(11) a carbonyl group substituted by a lower alkyl-piperazinyl group,
(12) an amino group optionally substituted by (a) a lower alkyl group, (b) a lower alkoxycarbonyl group, and (c) a lower alkanoyl group,
(13) a carbamoyl group optionally substituted by a group selected from (a) a lower alkyl group, (b) a lower alkoxy-lower alkyl group, (c) a lower alkyl group substituted by a hydroxyl group, and (d) a lower alkyl group substituted by a di-lower alkylamino group; and
(14) a group of the formula: —O—NH—C(=NH)NH$_2$; the "oxy group substituted by an optionally substituted saturated heterocyclic group" as a substituent for Ring B is an oxy group substituted by a saturated heterocyclic group optionally substituted by an aryl group; and the "substituted carbonyl group" as a substituent for Ring B is a carbonyl group substituted by a group selected from the followings:
(1) a lower alkoxy group,
(2) a hydroxyl group,
(3) an amino group optionally substituted by (a) a lower alkyl group, (b) a lower alkoxy group, (c) a lower alkoxy-lower alkyl group, (d) a hydroxy-lower alkyl group, (e) a lower alkyl group substituted by an amino group optionally substituted by a lower alkyl group, (f) a lower alkyl group substituted by an aryl group, and (g) a lower alkyl group substituted by a pyridyl group,
(4) a morpholinyl group, a pyrrolidinyl group, a piperidyl group or a thiomorpholinyl group,
(5) a hydroxypiperidyl group,
(6) a piperidyl group substituted by a hydroxy-lower alkyl group,
(7) a pyrrolidinyl group substituted by a hydroxy-lower alkyl group, and
(8) a lower alkyl-piperazinyl group;

the "optionally substituted amino group" as a substituent for Ring B is an amino group optionally substituted by a group selected from the followings:
(1) a lower alkyl group,
(2) a lower alkoxy-lower alkyl group,
(3) a hydroxy-lower alkyl group,
(4) a lower alkanoyl group,
(5) a lower alkoxy-lower alkanoyl group,
(6) a hydroxy-lower alkanoyl group,
(7) a lower alkanoyl group substituted by a lower alkanoyloxy group,
(8) a lower alkanoyl group substituted by an amino group optionally substituted by a group selected from (a) a lower alkyl group and (b) a lower alkanoyl group,
(9) a lower alkoxycarbonyl group,
(10) a lower alkoxycarbonyl group substituted by an aryl group,
(11) a carbamoyl group substituted by a lower alkyl group,
(12) a lower alkylsulfonyl group, and
(13) a lower alkylsulfonyl group substituted by a morpholinyl group.

Examples of saturated heterocyclic group includes a saturated 4- to 7-membered heterocyclic group containing 1 to 4 hetero atoms selected independently from the group consisting of nitrogen atom, oxygen atom and sulfur atom, specifically, imidazolidinyl, pyrazolidinyl, piperidyl, piperazinyl, morpholinyl, thiomorpholinyl, homopiperazinyl, homopiperidyl, pyrrolidinyl, oxazolidinyl or 1,3-dioxanyl.

Further examples include compounds wherein the group of the formula:

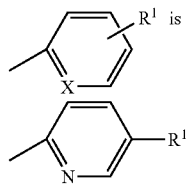

Ring B is

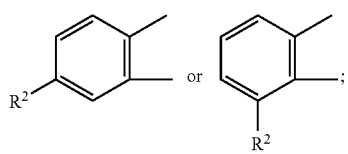

$R^1$ is a halogen atom or a lower alkyl group; and $R^2$ is a group selected from the followings:
A) a hydrogen atom,
B) a lower alkyl group optionally substituted by a group selected from the followings:
(1) a lower alkoxycarbonyl group,
(2) a carboxyl group,
(3) a carbamoyl group optionally substituted by a group selected from (a) a lower alkyl group, (b) a lower alkoxy-lower alkyl group, (c) a lower alkyl group substituted by a hydroxyl group, and (d) a lower alkoxy group,
(4) a carbonyl group substituted by a morpholinyl group,
(5) a piperidylcarbonyl group substituted by a hydroxy-lower alkyl group,
(6) a pyrrolidinylcarbonyl group substituted by a hydroxy-lower alkyl group,
(7) a carbonyl group substituted by a hydroxyl group-substituted piperidyl group, and
(8) a hydroxyl group;
C) a lower alkoxy group optionally substituted by a group selected from the followings:
(1) a carboxyl group,
(2) a lower alkoxycarbonyl group,
(3) a lower alkoxy group,
(4) a hydroxyl group,
(5) an aminooxy group optionally substituted by a lower alkoxycarbonyl group,
(6) a lower alkoxy group substituted by a lower alkoxy group,
(7) a carbonyl group substituted by a morpholinyl group, a piperidyl group or a pyrrolidinyl group,
(8) a carbonyl group substituted by a hydroxypiperidyl group,
(9) a piperidylcarbonyl group substituted by a hydroxy-lower alkyl group,
(10) a pyrrolidinylcarbonyl group substituted by a hydroxy-lower alkyl group,
(11) a carbonyl group substituted by a lower alkyl-piperazinyl group,

(12) an amino group optionally substituted by a group selected from (a) a lower alkyl group, (b) a lower alkoxycarbonyl group, and (c) a lower alkanoyl group,
(13) a carbamoyl group optionally substituted by a group selected from (a) a lower alkyl group, (b) a lower alkoxy-lower alkyl group, (c) a lower alkyl group substituted by a hydroxyl group, and (d) a lower alkyl group substituted by a di-lower alkylamino group, and
(14) a group of the formula: —O—NH—C(=NH)NH$_2$; and
D) a carbonyl group substituted by a group selected from the followings:
(1) a lower alkoxy group,
(2) a hydroxyl group,
(3) an amino group optionally substituted by a group selected from (a) a lower alkyl group, (b) a lower alkoxy group, (c) a lower alkoxy-lower alkyl group, (d) a hydroxy-lower alkyl group, (e) a lower alkyl group substituted by an amino group optionally substituted by a lower alkyl group, (f) a lower alkyl group substituted by an aryl group, and (g) a lower alkyl group substituted by a pyridyl group,
(4) a morpholinyl group, a pyrrolidinyl group, a piperidyl group or a thiomorpholinyl group,
(5) a hydroxypiperidyl group,
(6) a piperidyl group substituted by a hydroxy-lower alkyl group,
(7) a pyrrolidinyl group substituted by a hydroxy-lower alkyl group, and
(8) a lower alkyl-piperazinyl group.

Specific examples of the objective compounds of the manufacturing process of the present invention include:
trans-5-Dimethylaminocarbonyl-3-[4-(N-formyl-N-methylamino)cyclohexylcarbonylamino]-N-(5-chloropyridin-2-yl)benzofuran-2-carboxamide;
trans-3-[4-(N-acetyl-N-methylamino)cyclohexylcarbonylamino]-5-(2-hydroxyethyl)-N-(5-chloropyridin-2-yl) benzofuran-2-carboxamide;
trans-5-(morpholin-4-ylcarbonyl)-3-[4-(2-oxo-pyrroridin-1-yl)-cyclohexylcarbonylamino]-N-(5-chloropyridin-2-yl) benzofuran-2-carboxamide; and
trans-3-(4-dimethylaminocyclohexylcarbonylamino)-N-(5-chloropyridin-2-yl)benzofuran-2-carboxamide.

The pharmaceutically acceptable salt of the objective compound of the present invention includes a salt with an inorganic acid such as hydrochloric acid, hydrobromic acid, hydroiodic acid, sulfuric acid, nitric acid, phosphoric acid, etc.; a salt with an organic acid such as formic acid, acetic acid, propionic acid, oxalic acid, malonic acid, succinic acid, fumaric acid, maleic acid, lactic acid, malic acid, tartaric acid, citric acid, methanesulfonic acid, ethanesulfonic acid, p-toluenesulfonic acid, benzenesulfonic acid, etc.; salt with an acidic amino acid such as aspartic acid, glutamic acid, etc.; salt with a metal such as sodium, potassium, lithium, magnesium, calcium, aluminium, etc.; salt with an organic base such as methylamine, ethylamine, ethanolamine, etc.; or a salt with a basic amino acid such as lysine, ornithine, etc.

The objective compound of the present invention can be in the form of quaternary ammonium salt and includes a quaternary ammonium salt.

Further, the objective compound of the present invention includes an intramolecular salt, hydrate, solvate or crystalline polymorphism, etc.

Besides, when the objective compound of the present invention has a double bond(s), it may exist in the form of a geometrical isomer (cis, trans), when the objective compound of the present invention has an unsaturated bond such as carbonyl, it may exist in the from of a tautomerism, and when the objective compound of the present invention has an asymmetric carbon atom(s), it can exist as an optical isomer. The objective compound of the present invention encompasses these isomers and a mixture thereof.

Additionally, the objective compound of the present invention encompasses a prodrug of a compound as mentioned above. Examples of a prodrug include those prepared by protecting a functional group such as an amino or carboxy group of a compound above with a conventional protecting group.

The reaction between a compound of the formula [II] and a compound of the formula [III], and between a compound of the formula [II'] and a compound of the formula [III'] can be carried out under nitrogen in the presence of a catalyst, a ligand and a base in an appropriate solvent. Preferred leaving group usable includes a halogen atom and sulfonic acid ester residues such as an arylsulfonyloxy group, a lower-alkylsulfonyloxy group and a perhalogeno-lower-alkylsulfonyloxy group, and the like. As a catalyst, both of homogeneous and heterogeneous catalysts can be used. However, recoverable heterogenous catalysts are preferred in view of cost. Homogenous catalyst includes palladium acetate, etc., and heterogeneous catalyst includes a group VIII metal compound supported by a solid phase. Especially preferred catalyst is a group VIII metal compound supported by a solid phase which is a heterogeneous catalyst. The solid phase for the immobilized group VIII metal compound includes carbon and clay mineral, and the group VIII metal includes palladium and nickel. Palladium-carbon is especially preferred. As a ligand, diphenylphosphino compounds such as 2,2'-bis(diphenylphosphino)-1,1'-binaphthyl and 1,1'-bis(diphenylphosphino)ferrocene, triphenylphosphines and the like can be used preferably. As a base, both of inorganic and organic bases can be used. Examples of preferred organic base include triethylamine, N-methylmorpholine, N-methylpyrazine, tetramethylguanidine, pyridine, diisopropylethylamine, 1,8-diazabicyclo[5.4.0]undec-7-ene, 1,4-diazabicyclo[2.2.0] octane, and the like. Examples of preferred inorganic base include metal carbonate salts such as cesium carbonate and potassium carbonate, metal phosphate salts such as potassium phosphate, alkali metal hydroxide salts such as potassium hydroxide, alkali metal alkoxides such as sodium t-butoxide, and alkali metal acetates such as sodium acetate. Above all, inorganic bases are more preferred. As a solvent, any inert solvent which does not disturb the reaction can be used without limitation, and preferred examples include toluene, xylene and mesitylene. The reaction can be facilitated by mixing t-butyl alcohol as a solvent. It is preferred that the ratio of t-butyl alcohol to other solvent is about 1:4. The amount of a palladium catalyst used in the present reaction in relation to the compound [II] or [II'] is about 0.001-0.1 equiv., more preferably 0.04-0.06 equiv., and most preferably 0.04 equiv. The amount of a ligand used in the present reaction in relation to the compound [II] or [II'] is about 0.002-0.2 equiv., more preferably 0.08-0.16 equiv., and most preferably 0.08 equiv. The amount of a base used in the present reaction in relation to the compound [II] or [II'] is about 1-2 equiv., more preferably 1.4-2 equiv., and most preferably, 2 equiv. The present reaction can be carried out from a temperature of under cooling to under heating, specifically, at 0-200° C., preferably at 100-140° C.

Examples of aromatic ring of compound [II'] include carbocyclic aromatic rings having 6 to 24 ring carbons and heterocyclic aromatic rings having 5 to 24 ring carbons, specifically, benzene ring, naphthalene ring, indole ring, and the like. Examples of substituent therefor include an alkyl group, an aryl group, a cyano group, a nitro group, an optionally protected amino group, an alkoxy group, a carboxyl group, an alkoxycarbonyl group, a formyl group, an aryl group substituted by carboxyl group, and the like.

Examples of an optionally substituted amino group of the formula: $NR^4R^5$ include amino groups optionally substituted by a group selected from the followings:
(1) a lower alkyl group,
(2) a cycloalkyl group,
(3) a hydroxy-lower alkyl group,
(4) a 1,3-dioxanyl group substituted by a lower alkyl group,
(5) a lower alkyl group substituted by an amino group optionally substituted by a group selected from (a) a lower alkyl group, (b) a lower alkanoyl group, (c) a lower alkanoyl group substituted by an amino group substituted by a lower alkyl group, and (d) a lower alkoxycarbonyl group,
(6) a lower alkyl group substituted by a cyano group,
(7) a lower alkyl group substituted by a lower alkoxycarbonyl group,
(8) a lower alkyl group substituted by a carboxyl group,
(9) a lower alkyl group substituted by a carbamoyl group optionally substituted by a lower alkyl group,
(10) a lower alkyl group substituted by an aryl group,
(11) a lower alkyl group substituted by a pyridyl group,
(12) a lower alkoxycarbonyl group,
(13) a lower alkanoyl group substituted by a di-lower alkyl amino group,
(14) a lower alkanoyl group,
(15) a pyrimidinyl group,
(16) a lower alkanoyl group substituted by a morpholinyl group,
(17) a lower alkylsulfonyl group,
(18) a carbamoyl group substituted by a lower alkyl group,
(19) a carbonyl group substituted by an aryl group,
(20) a lower alkanoyl group substituted by a lower alkoxy group,
(21) a lower alkanoyl group substituted by a lower alkanoyloxy group,
(22) an aryl group substituted by a hydroxyl group, and
(23) a hydroxy-lower alkanoyl group; and examples of a nitrogen-containing heterocyclic group include a saturated or unsaturated 4- to 7-membered heterocyclic group containing at least one nitrogen atom, specifically, imidazolidinyl, pyrazolidinyl, piperidyl, piperazinyl, morpholinyl, thiomorpholinyl, homopiperazinyl, homopiperidyl, pyrrolidinyl, oxazolidinyl, 1,3-dioxanyl, and the like.

The reaction between a compound of the formula [IV] and a compound of the formula [V] can be carried out in the presence of a base in an appropriate solvent. Preferred leaving group includes a halogen atom and sulfonic acid ester residues such as an arylsulfonyloxy group, a lower-alkylsulfonyloxy group, a perhalogeno-lower-alkylsulfonyloxy group, and the like. As a base, alkali metal hydroxides such as sodium hydroxide, alkali metal carbonates such as sodium carbonate and organic amines such as N,N-diisopropylethylamine are preferred, and strongly-basic bases specifically alkali metal hydroxides such as sodium hydroxide are particularly preferred. As a solvent, any inert solvent which does not disturb the reaction can be used without limitation, and examples thereof include tetrahydrofuran, dimethylsulfoxide, a mixed solvent of toluene and water and a mixed solvent of ethyl acetate and water. A mixed solvent comprising water is more preferred. The mixed solvent contains water at the ratio of about 3 to 4, preferably about 4 in relation to an organic solvent. The amount of a base used in the present reaction in relation to the compound [IV] is 2-10 equiv., more preferably 3-5 equiv., and most preferably, 4 equiv. The present reaction can be carried out at a low temperature, for example, at 0-30° C.

The catalytic reduction of a compound of the formula [VI], [VI"], [VI'''] or [VI''''] can be carried out in the presence of a catalyst under hydrogen pressure in an appropriate solvent. Preferred catalyst is rhodium-carbon catalyst. As a solvent, any inert solvent which does not disturb the reaction can be used without limitation, and preferred examples include methanol, ethanol and water. The condition for hydrogen pressure used in the reaction is preferably low pressure, more preferably 7-30 atm, especially preferably 7-8 atm. The amount of a catalyst in relation to the compound [VI], [VI"], [VI'''] or [VI''''] is preferably 0.01-0.1 equiv., more preferably 0.015-0.03 equiv., and most preferably 0.015 equiv. The present reaction can be carried out from −20° C. to under heating, preferably from room temperature to 120° C.

The catalytic reduction of a compound of the formula [VI], [VI"], [VI'''] or [VI''''] sometimes requires pH control. In the case of compound [VI"], the condition is preferred to be neutral to basic conditions, more preferably weakly basic and most preferably pH 7-8. In the case of compound [VI''''], the condition is preferred to be neutral to acidic conditions, more preferably weakly acidic, and most preferably an acidic condition with acetic acid.

The lower-alkyl esterification of a compound of the formula [VII] wherein $COOR^0$ is a carboxyl group can be carried out in a conventional manner. For example, it can be carried out by treating a compound with a lower alkanol in an acidic condition of sulfuric acid, thionyl chloride, or the like in an appropriate solvent.

The isomerization of a compound of the formula [VII] or [VII"] can be carried out in the presence of a base in an appropriate solvent. As a base, alkali metal alkoxides such as sodium methoxide and potassium t-butoxide, alkali metal amides such as sodium hexamethyldisilazane, potassium hexamethyldisilazane, lithium hexamethyldisilazane and lithium diisopropylamide are preferred. As a solvent, any inert solvent which does not disturb the reaction can be used without limitation, and preferred examples include dimethylacetamide, methanol, ethanol, and ethers such as tetrahydrofuran and dioxane. The amount of a base used in the present reaction in relation to the compound [VII] or the compound [VII'] is about 1-2 equiv., more preferably 1.4-2 equiv., and most preferably, 2 equiv. In some cases, the reaction may be facilitated by adding a small amount of water. The present reaction can be carried out from a temperature of under cooling to under heating, for example, at −20-150° C., preferably at 0-80° C., more preferably at room temperature (0-30° C.).

The reaction proceeds in a favorable manner irrespective of the substituents for compound [VII']. As carboxylic acid derivatives of compound [VII'], esters, activated esters, acid halides, nitrites, amides, thiol esters, and the like can be used.

The cyanation of a compound of the formula [IX] or [IX'] can be carried out by treating a compound [IX] or [IX'] with a cyanizing agent in the presence of a catalyst, zinc and a ligand. Preferred leaving group includes a halogen atom and sulfonic acid ester residues such as an arylsulfonyloxy group, a lower-alkylsulfonyloxy group and perhalogeno-lower-alkylsulfonyloxy group, and the like. As a catalyst, both of homogeneous and heterogeneous catalysts can be used. However, recoverable heterogenous catalysts are preferred in view of cost. Homogenous catalyst includes palladium acetate, etc., and heterogeneous catalyst includes a group VIII metal compound supported by a solid phase. Especially preferred catalyst to be used is a group VIII metal compound supported by a solid phase which is a heterogeneous catalyst. The solid phase for an immobilized group VIII metal compound includes carbon and clay mineral, and the group VIII metal includes palladium and nickel. Palladium-carbon is especially preferred. As a ligand, phosphines such as triphenylphosphine, 1,1'-bis(diphenylphosphino)ferrocene, etc. can be used preferably. As a cyanizing agent, zinc cyanide, copper cyanide, potassium cyanide, sodium cyanide, acetone cyanohydrin, etc. can be used preferably. As a solvent, any inert solvent which does not disturb the reaction can be used without limitation, and preferred examples include dimethylacetamide, dimethylformamide and N-methylpyrrolidone. The amount of a palladium catalyst used in the present reaction in relation to the compound [IX] or [IX"] is about 0.001-0.1 equiv., more preferably 0.01-0.05 equiv., and most preferably 0.05 equiv. The amount of a ligand in relation to the compound [IX] or [IX'] is about 0.004-0.4 equiv., more preferably 0.04-0.2 equiv., and most preferably 0.2 equiv. The amount of zinc used in the present reaction in relation to the compound [IX] or [IX'] is about 0.1-1 equiv., more preferably 0.2-0.6 equiv., and most preferably 0.4 equiv. The present reaction can be carried out from a temperature of under cooling to under heating, specifically, at 0-200° C., preferably at 80-150° C.

The present reaction can be facilitated by activating zinc with an activating agent. Examples of such an activating agent include dibromoethane, bromine, iodine and tri-lower alkylsilyl halides such as trimethylsilyl chloride.

Examples of aromatic ring of compound [IX'] include carbocyclic aromatic ring having 6 to 24 ring carbons and heterocyclic aromatic ring having 5 to 24 ring carbons, specifically, benzene ring, pyridine ring, naphthalene ring, indole ring, and the like. Examples of substituent therefor include an alkyl group, an aryl group, a cyano group, a nitro group, an optionally protected amino group, an alkoxy group, a carboxyl group, an alkoxycarbonyl group, a formyl group, an aryl group substituted by carboxyl group, and the like.

The reaction between a compound of the formula [X] and a compound of the formula [XI] can be carried out in the presence of a halogenating agent and a base in an appropriate solvent. Preferred leaving group includes a halogen atom and sulfonic acid ester residues such as an arylsulfonyloxy group, a lower-alkylsulfonyloxy group, a perhalogeno-lower-alkylsulfonyloxy group, and the like. As an ester residue, lower alkyl residues such as methyl residue, ethyl residue, and the like are preferred. As a halogenating agent, alkali metal halides such as sodium iodide and sodium bromide are preferred. As a base, alkali metal carbonates such as potassium carbonate are preferred. As a solvent, any inert solvent which does not disturb the reaction can be used without limitation, and preferred examples include acetone. The present reaction can be carried out from room temperature to under heating, preferably, at 0-60° C.

Besides, the present reaction can be facilitated by carrying out in the presence of a phase-transfer catalyst and water. Preferred phase-transfer catalysts include tetramethylammonium chloride.

The reaction between a compound of the formula [XII] or [XII'] with a compound of the formula [XIII] can be carried out in the presence of a halogenating agent and a base in an appropriate solvent. As a halogenating agent, thionyl chloride, oxalyl chloride, and the like are preferred. As a base, organic amines such as triethylamine, pyridine, N-methylmorpholine, and the like are preferred. As a solvent, any inert solvent which does not disturb the reaction can be used without limitation, and preferred examples include methylene chloride. The present reaction can be carried out from room temperature to under heating, preferably, at 0-70° C.

Besides, the present reaction can proceed more preferably when a compound [XII] or [XII'] is firstly converted into a salt by addition of a weak base, then into an acid chloride by treatment with a halogenating agent before the reaction with a compound [XIII] in the presence of a base. Examples of such a weak base include N-methylmorpholine, N-methylpyrazine, tetramethylguanidine and the like, and the amount of a weak base used in relation to the compound [XII] or [XII'] is preferably one equivalent.

The cyclization of a compound of the formula [XIV] can be carried out in the presence of a base in an appropriate base. As a base, both of inorganic and organic bases can be used; however, an organic base is preferred. Examples of preferred organic base include triethylamine, N-methylmorpholine, N-methylpyrazine, tetramethylguanidine, pyridine, diisopropylethylamine, 1,8-diazabicyclo[5.4.0]undec-7-ene, 1,4-diazabicyclo[2.2.0]octane, and the like. Organic amines such as 1,8-diazabicyclo[5.4.0]undec-7-ene and strong organic bases such as sodium bis(trimethylsilyl)amide and the like are more preferred. Examples of preferred inorganic base include sodium carbonate, potassium hydroxide, and the like. As a solvent, any inert solvent which does not disturb the reaction can be used without limitation, and preferred examples include tetrahydrofuran. The amount of a base used in the present reaction in relation to the compound [XIV] is about 0.05-2.2 equiv., more preferably 1.2-2.2 equiv., and most preferably 1.2 equiv. The present reaction can be carried out from room temperature to under heating, specifically, at 0-100° C., preferably at 0-70° C.

The reaction between a compound of the formula [XV] and a compound of the formula [VIII] or a reactive derivative thereof can be carried out in the presence of a base in an appropriate solvent. Preferred examples of a base include organic bases such as pyridine, triethylamine, diisopropylethylamine, N-methylmorpholine, 1,8-diazabicyclo[5.4.0]undec-7-ene, 1,4-diazabicyclo[2.2.0]octane, and the like. As a reactive derivative of compound [VIII], acid halides corresponding thereto are preferred. As a solvent, any inert solvent which does not disturb the reaction can be used without limitation, and preferred examples include halogenated hydrocarbons such as methylene chloride and chloroform, tetrahydrofuran, and the like. The present reaction can be carried out from a temperature of under ice-cooling to under heating, preferably, at 15-25° C.

According to the reaction of the present invention wherein a compound of the formula [II'] is reacted with a compound of the formula [III'], an optionally substituted amino group or a nitrogen-containing heterocyclic group can be introduced to an aromatic ring in one step and at low cost.

According to the reaction of the present invention wherein a compound of the formula [IV] is reacted with a compound of the formula [V], a nitrogen-containing heterocyclic group can be introduced to benzene ring having a carboxyl group substantially in one step and at low cost.

According to the catalytic reduction of the present invention for a compound of the formula [VI"], [VI'''] or [VI''''], a compound of which cyclohexyl group has substituents at positions 1 and 4 can be prepared at low cost, which substituents are a carboxyl group and a group selected from an optionally substituted amino group and a nitrogen-containing heterocyclic group.

According to the isomerization of the present invention for a compound of the formula [VII"], a trans-form compound of which cyclohexyl group has substituents at positions 1 and 4 can be prepared at relatively low temperature, preferably from 0-80° C., more preferably at room temperature (0-30° C.) at low cost, which substituents are a carboxyl group and a substituent.

According to the cyanidation of the present invention for a compound of the formula [IX'], a cyano group can be introduced to an aromatic ring in one step at low cost.

According to the reaction of the present invention wherein the reaction between a compound of the formula [XII] or [XII'] and a compound of the formula [XIII] is conducted after forming a salt of the compound [XII] or [XII'] by addition of a weak base and then forming an acid chloride by treatment with a halogenating agent and then treating with a compound of the formula [XIII], an acid chloride of the compound [XII] or [XII"] can be prepared efficiently, which eventually makes it possible to produce a compound of the formula [XIV] in high yield.

According to the cyclization of the present invention for a compound of the formula [XIV], a compound of the formula [XV] can be prepared at relatively low temperature.

The term "lower" used in the definition of the formulas herein described means unless otherwise noted a straight- or branched-carbon chain having 1 to 6 carbon atoms.

Thus, examples of "lower alkyl group" include methyl, ethyl, propyl, isopropyl, butyl, isobutyl, s-butyl, t-butyl, pentyl, isopentyl, neopentyl, t-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, and the like. Among them, alkyl groups having 1 to 4 carbon atoms are preferred, and methyl, ethyl, propyl, isopropyl, butyl, isobutyl, s-butyl and t-butyl are especially preferred.

The term "lower alkoxy group" means a substituent wherein an oxygen atom is bound to the above-mentioned alkyl group. Among them, alkoxy groups having 1 to 4 carbon atoms are preferred, and methoxy, ethoxy, propoxy, isopropoxy, butoxy, isobutoxy, s-butoxy and t-butoxy groups are especially preferred.

Examples of "lower alkanoyl group" include alkanoyl groups formed by removing an "OH" group from carboxyl group of a lower carboxylic acid, specifically, formyl, acetyl, propionyl, butyryl, etc.

Examples of "halogen atom" include fluorine, chlorine, bromine and iodine atoms. Above all, fluorine, chlorine or bromine atom is preferred.

Examples of "aryl group" include phenyl or naphthyl group, preferably, phenyl group.

BEST MODE FOR CARRYING OUT THE INVENTION

The present invention will be illustrated in detail by Examples, but should not be construed to be limited thereto.

EXAMPLE 1

Pd/C (125 mg, 0.12 mmol) and 2,2'-bis(diphenylphosphino)-1,1'-binaphthyl (146 mg, 0.23 mmol) are suspended in a mixture of xylene (4 mL) and t-butyl alcohol (1 mL) under nitrogen. To the suspension are added methyl 4-chlorobenzoate (0.5 g, 2.93 mmol), 2-pyrrolidone (330 mL, 4.34 mmol) and potassium carbonate (0.8 g, 5.79 mmol), and the mixture is heated to reflux at 130° C.

Eighteen hours after the beginning of reflux, the reaction solution is cooled and insoluble materials are removed by filtration. The filtrate is neutralized with conc. hydrochloric acid (1.4 g) and the resulting solution is subjected to HPLC for quantitative analysis. As a result, it is confirmed that methyl 4-(2-pyrrolidon-1-yl)benzoate (0.62 g, 96.7%) is produced.

Mp: 120-121° C.

EXAMPLE 2

4-Aminobenzoic acid (100 g, 0.73 mol) is suspended in water (400 mL) and toluene (200 mL), and thereto is added dropwise 30% aqueous sodium hydroxide solution (97 g, 0.73 mol) under ice-cooling. After confirming that pH is basic enough, 4-chlorobutyric chloride (103 g, 0.73 mol) and 30% aqueous sodium hydroxide solution (290 g, 2.2 mol) are added dropwise simultaneously while maintaining the pH range of 9-12 and temperature range of 15-20° C. over 1 hour. After stirring at room temperature for 1 hour, sodium hydroxide (88 g, 2.2 mol) is added to the mixture under ice-cooling. To the reaction solution is added conc. hydrochloric acid (370 g) at 30° C. or below and precipitated crystals are collected by filtration. The resulting crystals are washed with water and air-dried at 40° C. to give 4-(2-pyrrolidon-1-yl)benzoic acid (144 g, yield: 96.0%, purity: 98.3%). The purity was determined by HPLC analysis.

Mp: 246-247° C.

EXAMPLE 3

4-(2-Pyrrolidon-1-yl)benzoic acid (4.0 g, 0.0195 mol), 5% rhodium-carbon catalyst (6.89 g, 1.5% mol) and methanol (200 mL) are charged in an autoclave (300 mL) and stirred at room temperature for 24 hours under hydrogen pressure (9 atm, conversion rate>99%, cis:trans=75:25). The reaction solution is concentrated to 100 ml, adjusted to pH 2 with conc. hydrochloric acid (11 g), and extracted with chloroform (100 mL) (×3). The organic layers are combined, washed with saturated brine (100 mL), dried over anhydrous magnesium sulfate, and concentrated under reduced pressure. The resulting crystals are collected with toluene, and air-dried at 50° C. overnight to give 4-(2-pyrrolidon-1-yl)cyclohexylcarboxylic acid (19.3 g, 93.7%, cis:trans=65:35).

EXAMPLE 4

To 4-(2-pyrrolidon-1-yl)cyclohexylcarboxylic acid are added ethanol (30 mL, 10V/W) and conc. sulfuric acid (0.4 g, 0.2 W/W), and the mixture is heated to reflux for 3.5 hours. After cooling the reaction solution to 10° C., sodium bicarbonate (powder) is thereto added. After foaming is stopped, ethanol is evaporated under reduced pressure. The residue is extracted with ethyl acetate and saturated brine. The resultant solution is dried over magnesium sulfate and evaporated to remove the solvent under reduced pressure to give ethyl 4-(2-pyrrolidon-1-yl)cyclohexylcarboxylate (oil, 2.3 g, 102%).

EXAMPLE 5

To ethyl 4-(2-pyrrolidon-1-yl)cyclohexylcarboxylate (5.0 g, mixture of cis and trans isomers, cis:trans=61:39) are added ethanol (25.0 mL, 5V/W) and sodium ethoxide (2.0 equiv. 0.0132 mol), and the mixture is stirred at room temperature for 20 hours. After adding water (5.0 mL, 1V/W), the reaction solution is stirred at room temperature for 2 hours, and evaporated to remove ethanol under reduced pressure. The residue is acidified by adding 2 N hydrochloric acid, and thereto is added an excessive amount of crystalline sodium chloride followed by extraction with methylene chloride. The extract is dried, and evaporated to remove the solvent under reduced pressure. The resulting crystals are collected with toluene to give 4-(2-pyrrolidon-1-yl)cyclohexylcarboxylic acid (2.9 g, trans:cis=88:12, yield 58%).

EXAMPLE 6

3-Bromo-4-hydroxybenzoic acid (50 g, 0.23 mmol) is suspended in methylene chloride, and thereto are added thionyl chloride (54.8 g, 0.46 mol) and dimethylformamide (0.92 mL, 0.0115 mol) successively at room temperature. The reaction solution is refluxed for one hour, and evaporated to remove the solvent under reduced pressure. The resultant is concentrated after adding methylene chloride (150 mL) to give the corresponding acid chloride. The so prepared acid chloride is dissolved in methylene chloride (250 mL), and thereto is added dropwise morpholine (100.4 g, 1.15 mol) while keeping the temperature below 15° C. under ice-cooling. After stirring for 2 hours, the solvent is concentrated under reduced pressure. To the concentration residue are added water (500 mL) and methylene chloride (10 mL), and the resulting suspension is adjusted to pH 1 to 2 with conc. hydrochloric acid (96 mL). The mixture is stirred for one hour under ice-cooling, and filtered to give crude crystals of 3-bromo-4-hydroxybenzoic acid (4-morpholinyl)amide (65.74 g, 99.9%). The crude crystals are suspended in methanol (329 mL) for 30 minutes under reflux, cooled gradually, stirred for one our under ice-cooling, and filtered to collect precipitated crystals to give 3-bromo-4-hydroxybenzoic acid (4-morpholinyl)amide (58.14 g, 88.4%). Mp: 216-218° C.

EXAMPLE 7

3-Bromo-4-hydroxybenzoic acid (4-morpholinyl)amide (286 mg, 1 mmol) is suspended in dimethylacetamide (2.9 mL), and thereto are added zinc cyanide (70 mg, 0.6 mmol), 10% Pd/C (53 mg, 0.05 mmol), zinc (36 mg, 0.56 mmol) and 1,1'-bis(diphenylphosphino)ferrocene (28 mg, 0.05 mmol), followed by deaeration under reduced pressure for nitrogen-displacement (×3). The reaction mixture is heated at 150-155° C. and stirred for 1 hour. After cooling, the insoluble materials are removed by filtration and the reaction solution is subjected to HPLC for quantitative analysis. As a result, it is obtained 3-cyano-4-hydroxybenzoic acid (4-morpholinyl) amide (203 mg, 87.4%). Mp: 238-240° C.

EXAMPLE 8

3-Cyano-4-hydroxybenzoic acid (4-morpholinyl)amide (232 mg, 1.0 mmol), sodium iodide (150 mg, 1.0 mmol), potassium carbonate (415 mg, 3.0 mmol) and chloroacetic acid (189 mg, 2.0 mmol) are suspended in acetone (12 mL) and refluxed for 5 hours. The reaction solution is evaporated to remove the solvent under reduced pressure, partitioned by adding water and ethyl acetate, and adjusted to pH=2-3 with hydrochloric acid. The aqueous layer is separated and re-extracted with ethyl acetate (×2). The solutions are combined and washed with saturated brine. The organic layer is dried over magnesium sulfate, and evaporated to remove the solvent under reduced pressure. The precipitated crude crystals are suspended in methanol-diethyl ether, and filtered to give 3-cyano-4-carboxymethoxybenzoic acid (4-morpholinyl) amide (241 mg, 83%). Mp: 205-206° C.

EXAMPLE 9

3-Cyano-4-carboxymethoxybenzoic acid (4-morpholinyl) amide (150 mg, 0.517 mmol) is suspended in toluene (3 mL) and chloroform/amylene (3 mL), and thereto are added thionyl chloride (615 mg, 5.17 mmol) and dimethylformamide (2 drops) successively at room temperature. The reaction solution is stirred at 70° C. for one hour, and evaporated to remove the solvent under reduced pressure to give the corresponding acid chloride. The so prepared acid chloride is dissolved in methylene chloride (3 mL), and thereto is added dropwise a suspension of 6-amino-3-chloropyridine (66 mg, 0.517 mmol) and triethylamine (0.15 ml, 1.03 mmol) in methylene chloride (1 mL) under ice-cooling. After stirring for 1.5 hours, the solvent is concentrated under reduced pressure. The concentration residue is suspended in water and acetone, and the precipitated crystals are collected by filtration to give 3-cyano-4-(5-chloropyridin-2-ylaminocarbonyl-methoxy) benzoic acid (4-morpholinyl)amide (141 mg, 68%). Mp: 165-167° C.

EXAMPLE 10

3-Cyano-4-(5-chloropyridin-2-ylaminocarbonylmethoxy) benzoic acid (4-morpholinyl)amide (10 g) is suspended in tetrahydrofuran (50 ml) at room temperature, and thereto is added dropwise 1,8-diazabicyclo[5.4.0]undec-7-ene (4.56 g). The mixture is warmed to 70° C., and stirred for 2 hours. After confirming the completion of reaction, the reaction mixture is cooled to room temperature, and thereto is added dropwise water (150 mL) at 30° C. or below, followed by stirring at room temperature for 30 minutes. The precipitated crystals are collected by filtration, washed with water, and dried at 50° C. to give 3-amino-5-(morpholinyl-4-ylcarbonyl)-N-(5-chloropyridin-2-yl)benzofuran-2-carboxamide (yield: 7.87 g, 78.7%). Mp: 244-245° C.

EXAMPLE 11 trans-4-(2-Pyrrolidon-1-yl)cyclohexylcarboxylic acid (2.37 g) is suspended in chloroform (9 ml) under ice-cooling, and thereto is added dropwise thionyl chloride (2.00 g), followed by stirring at 10° C. for 15 minutes. After confirming the disappearance of starting material, the reaction solution is evaporated under reduced pressure to give an acid chloride of trans-4-(2-pyrrolidon-1-yl)cyclohexylcarboxylic acid. Separately, 3-amino-5-(morpholinyl-4-ylcarbonyl)-N-(5-chloropyridin-2-yl)benzofuran-2-carboxamide (3.00 g) is suspended in pyridine (21 ml) under ice-cooling. To the suspension is added dropwise a suspension of previously prepared acid chloride of trans-4-(2-pyrrolidon-1-yl)cyclohexylcarboxylic acid in chloroform (10 ml). After the mixture is stirred at room temperature for 20 hours and the completion of reaction is confirmed, the reaction solution is poured into water, followed by extraction with ethyl acetate. After evaporating the extract, methanol is added for crystallization, and air-dried at 50° C. to give trans-5-(morpholin-4-ylcarbonyl)-3-[4-(2-oxo-pyrrolidin-1-yl)cyclohexylcarbonylamino]-N-(5-chloropyridin-2-yl)benzofuran-2-carboxamide (2.74 g, yield: 61.6%). Mp: 253-255° C.

EXAMPLE 12 trans-4-(2-Pyrrolidon-1-yl)cyclohexylcarboxylic acid (20.0 g) is suspended in dichloromethane (100 ml) at room temperature, and thereto is added dropwise thionyl chloride (10.1 g), followed by stirring at room temperature for 30 minutes. After confirming the disappearance of starting material, the reaction solution is evaporated under reduced pressure to give acid chloride of trans-4-(2-pyrrolidon-1-yl)cyclohexylcarboxylic acid, Separately, 3-amino-5-(morpholinyl-4-ylcarbonyl)-N-(5-chloropyridin-2-yl)benzofuran-2-carboxamide (20.0 g) is suspended in pyridine (140 ml), and thereto is added dropwise a suspension of previously prepared acid chloride of trans-4-(2-pyrrolidon-1-yl)cyclohexylcarboxylic acid in dichloromethane (100 ml). After the mixture is stirred at room temperature for about 1 hour and the completion of reaction is confirmed, the reaction solution is partitioned by adding water (200 ml). The extract is washed, and the organic layer is evaporated under reduced pressure to give a concentration residue of trans-5-(morpholin-4-ylcarbonyl)-3-[4-(2-oxo-pyrrolidin-1-yl)cyclohexylcarbonylamino]-N-(5-chloropyridin-2-yl)benzofuran-2-carboxamide. The residue is crystallized with 80% aqueous ethanol (48 ml), and crystals are collected by filtration to give wet crystals of trans-5-(morpholin-4-ylcarbonyl)-3-[4-(2-oxo-pyrrolidin-1-yl)cyclohexylcarbonylamino]-N-(5-chloropyridin-2-yl)benzofuran-2-carboxamide monohydrate. The wet materials are dried at 80° C. to give trans-5-(morpholin-4-ylcarbonyl)-3-[4-(2-oxo-pyrrolidin-1-yl)cyclohexylcarbonylamino]-N-(5-chloropyridin-2-yl)benzofuran-2-carboxamide(anhydride) (3.9 g, yield: 65.8%).

Aldehyde: Mp: 253-255° C.

IR (KBr, cm$^{-1}$): 1646, 1306, 1110

Monohydrate: IR (KBr, cm-1): 1646, 1303

EXAMPLE 13

Palladium-carbon (125 mg, 0.12 mmol) and (±)-2,2'-bis(diphenylphosphino)-1,1'-binaphthyl (146 mg, 0.23 mmol) are suspended in a mixture of xylene (4 mL) and t-butyl alcohol (1 mL) under nitrogen. To the suspension are added methyl 4-chlorobenzoate (0.5 g, 2.93 mmol), 2-piperidone (436 mg, 4.40 mmol) and potassium carbonate (0.81 g, 5.86 mmol), and the mixture is heated to reflux at 130° C. After 48 hours from the beginning of reflux, the reaction solution is cooled and the insoluble materials are removed by filtration. The resulting solution is subjected to HPLC for quantitative determination of product. As a result, it is confirmed that methyl 4-(2-piperidon-1-yl)benzoate (0.40 g, 59.1%) is produced. Mp: 118.6° C.

EXAMPLE 14

(1) Ethyleneglycol mono 2-chloroethyl ether (10 g, 0.08 mol) is added to an aqueous 30% hydrogen peroxide solution (22.8 g, 0.2 mol) and thereto are added sodium tungustate dihydrate (0.53 g, 1.6 mmol) and trioctylmethylammonium sulfate (0.75 g, 1.6 mmol). The mixture is stirred at 90° C. for 4 hours. After adding aqueous sodium thiosulfate solution, the mixture is extracted with ethyl acetate (50 mL). The organic layers are combined, washed, dried and concentrated to give oily residue (9 g). The residue is diluted with diethyl ether, and the insoluble materials are removed by filtration. The filtrate is partitioned by adding aqueous sodium bicarbonate. The aqueous layer is washed with diethyl ether and acidified with dilute hydrochloric acid, followed by extraction with ethyl acetate. The organic layers are combined, dried, and concentrated to give 2-chloroethoxyacetic acid (2.14 g, crude, 19.3%) as oily residue.

IR: ν=3410, 1727, 1123, 1044 cm$^{-1}$ (2) 2-Chlorethoxyacetic acid (1.11 g, 8 mmol) is dissolved in dichloromethane (22 mL), and thereto are added thionyl chloride (1.17 mL, 16 mmol) and dimethylformamide (30 μL, 0.4 mmol) successively at room temperature. After stirring at room temperature for 2.5 hours, the mixture is concentrated, and the residue is dissolved in dichloromethane (22 mL). To the mixture are added methyl 4-aminobenzoate (661 mg, 4 mmol) and pyridine (674 μL, 8 mmol) under ice-cooling, followed by stirring overnight. The reaction solution is washed with dilute hydrochloric acid, dried, and concentrated. The residue is subjected to silica gel column chromatography to give ethyl 4-(2-chloroethoxyacetylamino)benzoate (540 mg, 23.6%).

(3) Ethyl 4-(2-Chroloethoxyacetylamino)benzoate (420 mg, 1.47 mmol) is dissolved in tetrahydrofuran (42 mL), and thereto is added sodium hydride (56.3 mg, 1.47 mmol) under ice-cooling. After stirring at 0° C. for 3.5 hours, dilute hydrochloric acid is added to the mixture, followed by concentration. The residue is dissolved in ethyl acetate and washed with water. The aqueous layer is re-extracted with ethyl acetate, combined, and dried. After concentration, the residue is crystallized from diethyl ether/hexane to give ethyl 4-(3-oxomorpholinyl)benzoate (233 mg, 62.1%). The mother liquid is concentrated and subjected to preparative TLC to give ethyl 4-(3-oxomorpholinyl)benzoate (35.1 mg, 9.4%).

IR: ν=1706, 1664, 1606 cm$^{-1}$

MS: m/z=250 [(M+1)$^+$]

(4) Ethyl 4-(3-oxomorpholinyl)benzoate (35.1 mg, 0.141 mmol) and 5% rhodium-carbon catalyst (22 mg, 7.05 μmol) are suspended in ethanol (3 mL), and stirred at 80° C. for 3 hours under hydrogen pressure (7 bar). The catalysts are removed by flirtation, and the filtrate is concentrated under reduced pressure to give ethyl 4-(3-oxomorpholinyl)cyclohexanecarboxylate (35.1 mg, 97.6%).

(5) To a solution of ethyl 4-(3-oxomorpholinyl)cyclohexanecarboxylate in tetrahydrofuran (150 μL) is added potassium t-butoxide (13.5 mg, 0.121 mmol) previously suspended in a solution of water (2.2 mg, 0.121 mmol) in tetrahydrofuran (150 μL) under ice cooling, and the mixture is stirred for 5.5 hours while elevating the temperature gradually. The mixture is neutralized with an aqueous dilute hydrochloric acid and partitioned by adding water (1 mL) and ethyl acetate (1 mL). The aqueous layer is re-extracted with ethyl acetate (1 mL) (×2). The organic layers are combined, dried, and concentrated to give crystalline residue (12.5 mg, yield 91.2%, trans/cis=>95/5 as confirmed by NMR). The residue is crystallized by adding ethyl acetate and hexane to give trans-4-(3-oxomorpholinyl)cyclohexanecarboxylic acid (5.6 mg, 40.9%). Mp: 200-201° C.

EXAMPLE 15

(1) To 4-(2-pyrrolidon-1-yl)benzoic acid are added methanol (1.0 g, 0.2 W/W) and conc. sulfuric acid (1.0 g, 0.2 W/W), and the mixture is heated to reflux for 18 hours. After confirming the completion of the reaction by TLC, the reaction solution is cooled to 10° C., adjusted to pH 7.2 with aqueous 30% sodium hydroxide solution, and evaporated to remove methanol under reduced pressure. To the residue is added water, and crystals are collected by filtration and washed with cold water (50 mL). The crystals are air-dried at 50° C. to give methyl 4-(2-pyrrolidon-1-yl)benzoate (4.92 g, 0.0218 mol, 92.1%). Mp: 120-121° C.

(2) Methyl 4-(2-pyrrolidon-1-yl)benzoate (21.4 g, 0.098 mol), 5% rhodium-carbon catalyst (6.89 g, 1.5% mol) and methanol (200 mL) are charged in an autoclave (1 L) and stirred at room temperature for 24 hours under hydrogen pressure (9 atm). The reaction solution is cooled, filtered to collect the catalysts, and washed with methanol. The filtrate is evaporated to remove the solvent under reduced pressure, and re-concentrated by adding toluene to give methyl 4-(2-pyrrolidon 1-yl)cyclohexanecarboxylate as a mixture of cis and trans isomers (22.0 g, 100%, hemicryastals, cis:trans=67:33).

EXAMPLE 16

(1) 4-(2-Pyrrolidon-1-yl)benzoic acid (3 g, 0.015 mol) is suspended in ethanol (30 ml), and thereto is added dropwise thionyl chloride (1.07 mL, 0.015 mol) at room temperature, followed by heating to reflux for 3 hours. After confirming the completion of the reaction by TLC, the reaction solution is concentrated to give residue (3.63 g, 106%), The residue is re-crystallized from a mixture of n-hexane-ethyl acetate to give ethyl 4-(2-pyrrolidon-1-yl) benzoate (1.54 g, yield 45.2%). Mp: 94-95° C.

(2) Ethyl 4-(2-pyrrolidon-1-yl)benzoate (583 mg, 2.5 mmol), 5% rhodium-carbon catalyst (178 mg, 1.5% mol, 56.7% wet material) and ethanol (10 mL) are charged in a small reducing device and stirred at room temperature for 24 hours under hydrogen pressure (7 atm). The reaction solution is cooled, filtered to collect the catalysts, and washed with ethanol. The filtrate is evaporated to remove the solvent under reduced pressure, and re-concentrated by adding toluene to give ethyl 4-(2-pyrrolidon-1-yl)cyclohexanecarboxylate as a mixture of cis and trans isomers (600 mg, yield 100%, crystals of low-melting point, cis:trans=63:37).

EXAMPLE 17

4-(2-Pyrrolidon-1-yl)benzoic acid (20 g, 0.097 mol), 5% rhodium-carbon catalyst (6.89 g, 1.5% mol) and methanol (200 mL) are charged in an autoclave (300 mL) and stirred at room temperature for 24 hours under hydrogen pressure (9 atm, conversion rate >99%, cis:trans=75:25). The reaction solution is concentrated to 100 ml, and adjusted to pH 2 with conc. hydrochloric acid (11 g), followed by extraction with chloroform (100 mL) (×3). The organic layers are combined, washed with saturated brine (100 mL), dried over anhydrous magnesium sulfate, and the insoluble materials are removed by filtration. The resultant solution is evaporated to remove the solvent under reduced pressure. To the residue is added toluene and the precipitated crystals are collected by filtration, air-dried at 50° C. overnight to give 4-(2-pyrrolidon-1-yl)cyclohexylcarboxylic acid (19.3 g, 93.7%, cis:trans=65:35).

EXAMPLE 18

4-(2-Pyrrolidon-1-yl)benzoic acid (4.0 g, 0.0195 mol), 5% rhodium-carbon catalyst (2.8 g, 3.0% mol) and methanol (80 mL) are charged in an autoclave (300 mL) and stirred at room temperature for 5 hours under hydrogen pressure (50 atm, conversion rate >99%, cis:trans=50:50). The reaction solution is cooled, filtrated to collect the catalysts, and washed with methanol. The filtrate is concentrated under reduced pressure, and the resulting crystals are washed with methanol to give 4-(2-pyrrolidon-1-yl)cyclohexylcarboxylic acid as a mixture of cis and trans isomers (3.4 g, 82.5%, cis:trans=79:21). A portion (3.0 g) is dissolved in methanol (15 mL) under heating, and cooled. The resulting crystals are washed with cooled methanol to give cis-4-(2-pyrrolidon-1-yl)cyclohexylcarboxylic acid (700 mg, >99% de). The tertiary structure of cis-4-(2-pyrrolidon-1-yl)cyclohexylcarboxylic acid was confirmed by X-ray structure analysis. Mp: 188° C.

EXAMPLE 19

(1) To 4-(2-pyrrolidon-1-yl)cyclohexylcarboxylic acid (3.0 g, 0.014 mol) are added methanol (30 mL, 10 V/W) and conc. sulfuric acid (0.3 g, 0.1 W/W), and the mixture is heated to reflux for 18 hours. After confirming the completion of the reaction by HPLC, the reaction solution is cooled to 10° C. To the solution is added sodium bicarbonate (powder), and after foaming is stopped, evaporated to remove methanol under reduced pressure. The residue is extracted with ethyl acetate and saturated brine. The extract is treated with magnesium sulfate, concentrated under reduced pressure, and the resulting crystals are collected with hexane. The crystals are air-dried at 50° C. to give methyl 4-(2-pyrrolidon-1-yl)cyclohexylcarboxylate (2.78 g, 86.9%).

(2) To methyl 4-(2-pyrrolidon-1-yl)cyclohexylcarboxylate (1.0 g, 0.0044 mol, a mixture of cis and trans isomers, cis:trans=72:28) are added methanol (5.0 mL, 5V/W) and sodium methoxide (28% in MeOH, 2.57 g), and the mixture is heated to reflux for 3 hours. The reaction solution is cooled to room temperature, and thereto is added water (0.5 mL), followed by stirring at room temperature for 30 minutes. The mixture is then adjusted to pH 1-2 with conc. hydrochloric acid, and evaporated to remove methanol under reduced pressure. After adding water to the residue, crystals are collected by filtration and washed with cold water (20 mL). The crystals are air-dried at 50° C. to give crude crystals (900 mg, 0.00425 mol, 95.6%, cis:trans=12:88). The crude crystals are dissolved in water (6 mL) and methanol (1 mL) under heating, and then the mixture is cooled. The resulting crystals are collected by filtration to give trans-4-(2-pyrrolidon-1-yl)cyclohexylcarboxylic acid (625 mg, >99% de).

IR: ν=2935, 1716, 1633 $cm^{-1}$ (3) Methyl 4-(2-pyrrolidon-1-yl)cyclohexylcarboxylate (1.4 g, 0.0062 mol, cis:trans=1:2) is dissolved in dimethylacetamide, and thereto is added sodium hexamethyldisilazane (1.0 M in tetrahydrofuran, 7.5 mL) at room temperature, followed by stirring for one hour. To the reaction solution is added water (1.4 mL), and the mixture is stirred at room temperature for 10 minutes, and the reaction solution is subjected to HPLC for quantitative analysis. As a result, it is obtained trans-4-(2-pyrrolidon-1-yl)cyclohexylcarboxylic acid (1.37 g, 0.0065 mol, cis:trans=2:98, 103%).

EXAMPLE 20

(1) To 4-(2-pyrrolidon-1-yl)cyclohexylcarboxylic acid (2.0 g, 0.0095 mol) are added ethanol (30 mL, 10 V/W) and conc. sulfuric acid (0.4 g, 0.2 W/W), and the mixture is heated to reflux for 3.5 hours, then the completion of reaction is confirmed by HPLC. The reaction solution is cooled to 10° C. and thereto is added sodium bicarbonate (powder). After foaming is stopped, the mixture is concentrated to remove ethanol under reduced pressure. The residue is extracted with ethyl acetate and saturated brine. The extract is treated with magnesium sulfate, and concentrated under reduced pressure to give ethyl 4-(2-pyrrolidon-1-yl)cyclohexylcarboxylate (oil, 2.30 g, 101.5%).

(2) To ethyl 4-(2-pyrrolidon-1-yl)cyclohexylcarboxylate (1.0 g, 0.0044 mol, cis:trans=72:28) are added ethanol (5.0 mL, 5V/W) and sodium ethoxide (0.90 g, 0.013 mol), and the mixture is stirred at room temperature for 18 hours. The reaction solution is subjected to HPLC for quantitative analysis. As a result, it is obtained trans-4-(2-pyrrolidon-1-yl)cyclohexylcarboxylic acid (746 mg, 0.0035 mol, 80.5%).

EXAMPLE 21

(1) To 4-(2-pyrrolidon-1-yl)cyclohexylcarboxylic acid (21.1 g, 0.10 mol, trans:cis=45:55) are added ethanol (105.5 mL, 5V/W) and thionyl chloride (13.1 g, 0.11 mol), and the mixture is heated to reflux for one hour. The reaction solution is cooled to room temperature, and evaporated under reduced pressure. To the residue is added water, and extracted with chloroform. The aqueous layer is re-extracted with chloroform, and the organic layers are combined, washed with saturated aqueous sodium bicarbonate and saturated brine successively, and dried over magnesium sulfate to give a solution of ethyl 4-(2-pyrrolidon-1-yl)cyclohexylcarboxylate. Magnesium sulfate is removed by filtration and the resultant solution is divided equally. A quarter portion is used in the next step.

(2) The solution of ethyl 4-(2-pyrrolidon-1-yl)cyclohexylcarboxylate above is concentrated under reduced pressure, and thereto are added tetrahydrofuran (18 mL) and water (900 mg, 0.05 mol). The resulting solution is added dropwise to a suspension of potassium t-butoxide (5.6 g, 0.05 mol) in tetrahydrofuran (18 mL) at room temperature. After 30 minutes, the disappearance of ethyl 4-(2-pyrrolidon-1-yl)-cyclohexylcarboxylate is confirmed (the composition ratio in the reaction solution of trans:cis=93:7). To the reaction solution is added water. The solution is neutralized with hydrochloric acid, and evaporated to remove tetrahydrofuran under reduced pressure. To the concentration residue is added brine, followed by extraction with methylene chloride. The organic layers are washed with saturated brine, dried over magnesium sulfate, and evaporated under reduced pressure to give solid materials. The solid materials are subjected to warm extraction with toluene, filtered, and air-dried to give trans-4-(2-pyrrolidon-1-yl)cyclohexylcarboxylic acid (4.31 g, yield: 82.0% from (1), trans:cis=97.4:2.6).

EXAMPLE 22

(1) Ethyl 4-aminobenzoate (33.0 g, 0.20 mol), 5% rhodium-carbon catalyst (16 g, 1.5% mol), ethanol (330 mL) and acetic acid (16 mL) are charged in an autoclave (1 L) and stirred at 80° C. for 20 hours under hydrogen pressure (7 atm). The reaction solution is cooled, filtered to remove the catalysts, and washed with methanol (110 mL). The filtrate is concentrated under reduced pressure to give ethyl 4-aminocyclohexanecarboxylate as a mixture of cis and trans isomers.

(2) To the residue of ethyl 4-aminocyclohexanecarboxylate (Net 33 g, 0.2 mol) obtained in (1) above is dissolved in toluene (165 mL) and water (165 mL), and thereto is added sodium carbonate (31.8 g, 0.3 mol). Benzyloxycarbonyl chloride (34.1 g, 0.2 mol) is added dropwise to the mixture at 10° C. or below over 30 minutes, and thereto is added water to dissolve the resulting salts, whereby the solution is partitioned. The aqueous layer is re-extracted with ethyl acetate. The organic layers are combined, dried over magnesium sulfate, and concentrated to give ethyl 4-benzyloxycarbonylaminocyclohexanecarboxylate (60.17 g, yield: 98.5%) as oil.

IR: ν=3346, 1710 cm$^{-1}$
MS: m/z=306 [(M+1)$^+$]

(3) To tetrahydrofuran (111 mL) is added potassium t-butoxide (11.22 g, 0.103 mol) under ice-cooling, and thereto is added dropwise a solution of ethyl 4-benzyloxycarbonylaminocyclohexanecarboxylate (15.79 g, 0.0517 mol) in tetrahydrofuran (32 mL) at 10° C. or below. A solution of water (1.8 g, 0.103 mol) in tetrahydrofuran (79 mL) is then added dropwise at 5° C. over 40 minutes. After 2 hours, the reaction mixture is neutralized with 10% hydrochloric acid (35 mL), and evaporated to remove tetrahydrofuran. To the residue are added ethyl acetate (100 mL), tetrahydrofuran (30 mL), 10% hydrochloric acid (2 mL) and water (80 mL), and the mixture is heated at 50° C., and separated. The aqueous layer is re-extracted with ethyl acetate (80 mL), and the organic layers are combined, dried over magnesium sulfate, and concentrated (trans/cis=86:14). To the residue are added isopropyl alcohol (32 mL) and isopropyl ether (128 mL) to precipitate crystals. The crystals are collected by filtration, and dried to give trans-4-benzyloxycarbonylaminocyclohexanecarboxylic acid (7.31 g, 52.7%, trans/cis=99.9:0.1).

IR: ν=3306, 1684, 1541 cm$^{-1}$
MS: m/z=278 [(M+1)$^+$]

EXAMPLE 23

(1) Ethyl 4-t-butoxycarbonylaminobenzoate (33.0 g, 0.20 mol), 5% rhodium-carbon catalyst (16 g, 1.5% mol), ethanol (50 mL) and acetic acid (16 mL) are charged in an autoclave (300 mL) and stirred at 80° C. for 5 hours under hydrogen pressure (10 atm). The reaction solution is cooled, and filtered to remove catalysts, and washed with ethanol (20 mL). The filtrate is concentrated under reduced pressure to give ethyl 4-t-butoxycarbonylaminocyclohexanecarboxylate as a mixture of cis and trans isomers.

(2) To tetrahydrofuran (40 mL) is added potassium t-butoxide (4.22 g, 37.6 mmol) under ice-cooling, and thereto is added dropwise a solution of ethyl 4-t-butoxycarbonylaminocyclohexanecarboxylate (5.07 g, 18.8 mmol) in tetrahydrofuran (16 mL) at 10° C. or below. To the mixture is added dropwise a solution of water (0.68 g, 37.6 mmol) in tetrahydrofuran (66 mL) at −10° C. over 55 minutes. After warming gradually to room temperature, the mixture is stirred for 22 hours, neutralized with 10% aqueous hydrochloric acid solution (14 mL), and evaporated to remove tetrahydrofuran. To the residue are added dichloromethane (50 mL), 10% hydrochloric acid (2 mL) and water (50 mL), whereby the solution is separated. The aqueous layer is re-extracted with dichloromethane (50 mL). The organic layers are combined, dried over magnesium sulfate, and concentrated (trans/cis=83:17). To the residue are added ethyl acetate (2.5 mL) and isopropyl ether (15 mL) to precipitate crystals. The crystals are collected by filtration and dried to give trans-4-Boc aminocyclohexanecarboxylic acid (2.94 g, 64.3%, trans/cis=99.9:0.1). The mother liquid is concentrated, and thereto are added ethyl acetate (0.5 mL) and isopropyl ether (10 mL) to precipitate crystals. The crystals are collected by filtration, and dried to give the second crops (0.83 g, 18.2%, trans/cis=40:60).

IR: ν=1683, 1516 cm$^{-1}$
MS: m/z=244 [(M+1)$^+$]

EXAMPLE 24

4-Hydroxybenzoic acid (10 g, 0.72 mol) is suspended in ethyl acetate (100 mL, 10 V/W), and thereto is added dropwise bromine (11.6 g, 0.072 mol) at room temperature. After stirring at room temperature for 19 hours, the reaction solution is concentrated to give crystalline residue (white). To the resulting residue is added methylene chloride, and then thionyl chloride (12.9 g, 0.109 mol) and dimethylformamide (0.26 g, 0.004 mol) successively at room temperature. The reaction solution is heated to reflux for 1.5 hours, and evaporated to remove the solvent under reduced pressure to give the corresponding acid chloride. The so prepared acid chloride is dissolved in methylene chloride (79 mL, 8V), and thereto is added dropwise morpholine (15.8 g, 0.181 mol) at 20° C. or below under ice-cooling. After confirming the completion of the reaction, the solvent is concentrated under reduced pressure. To the concentration residue is added water (31 mL, 3.1V/W) and concentrated under reduced pressure. After confirming that the organic solvent is not evaporated, the residue is suspended by adding methanol (79 mL, 8V), and adjusted to pH 2 with 10% hydrochloric acid. The suspension is stirred for 2 hours under ice-cooling and the precipitated crystals are collected by filtration. The crystals are washed with water until pH of filtrate becomes neutral, and dried at 50° C. under reduced pressure to give 3-bromo-4-hydroxybenzoic acid (4-morpholinyl)amide (16.8 g, 81.3%, theoretical yield: 20.72 g, purity: 98.7 area %, content: 97.5%). Mp: 216-218° C.

EXAMPLE 25

3-Bromo-4-hydroxybenzoic acid (4-morpholinyl)amide (150 g, 0.524 mol), zinc cyanide (44.23 g, 0.341 mmol), zinc (0.90 g, 14 mmol) and 5% palladium-carbon (44.6 g, 0.021 mmol) are suspended in dimethylacetamide (1500 mL), and bubbled with nitrogen for 35 minutes. After further adding triphenylphosphine (22.0 g, 0.084 mmol) under nitrogen, the reaction mixture is heated at 120° C., and stirred for 4 hours. The mixture is cooled to 25° C., stirred overnight, and the insoluble materials are separated by filtration at room temperature. The active carbon is washed with dimethylacetamide (1V, 150 mL). In the following procedures, an aliquot is used, which is obtained by dividing the solution above equally into five aliquots. The solvent is evaporated so that 2V of dimethylacetamide remains. After adding toluene (180 mL 6V), conc. hydrochloric acid (0.71 w, 21.3 g) is added dropwise at 30° C. or below and bubbled with nitrogen at 25° C. for one hour. Toluene is evaporated until the concentration of hydrogen cyanide becomes 50 ppm or less (20 mmHg). After adding water (5.4V, 163 mL), 37% formalin (17 mL, 2 equiv.) is added at room temperature. The mixture is stirred overnight, and the amount of hydrogen cyanide in the gas phase is confirmed to be 5 ppm on a detection tube. After adding 37% formalin (17 mL, 2 equiv.), the mixture is stirred at 35° C. for one hour, and the amount of hydrogen cyanide in the gas phase is confirmed to be 1 ppm or below on a detection tube. The mixture is ice-cooled (4° C.) for one hour. The crystals are collected by filtration, washed with water (6V, 180 mL), aqueous 5% sodium bicarbonate (1V, 30 ml), and then water (2 v, 60 ml) (pH=7). The wet materials are suspended into acetone (1.5 V, 45 mL), stirred for 0.5 hours under reflux, cooled gradually, stirred at 5° C. for one hour under ice-cooling, and filtered. The resulting crystals are washed with 0.5V of acetone (15 mL), and dried with a conical dryer to give 3-cyano-4-hydroxybenzoic acid (4-morpholinyl)amide (20.06 g, yield: 82.4%, content: 98.1%). Mp: 238-240° C.

EXAMPLE 26

Zinc powder (78 mg, 1.2 mmol) is suspended into dimethylacetamide (5.7 mL), and thereto is added bromine (20 µl, 0.4 mmol) at room temperature under nitrogen. The mixture is stirred until the color of bromine disappears (15-25 分), and thereto are added 3-bromo-4-hydroxybenzoic acid (4-morpholinyl)amide (572 mg, 2 mmol), zinc cyanide (118 mg, 1.0 mmol), 5% palladium-carbon (170 mg, 0.08 mmol) and triphenylphosphine (84 mg, 0.32 mmol). The vacuum deaeration and the nitrogen introduction are repeated five times. The mixture is heated at 120° C. (internal temperature) for one hour, when the inversion rate is confirmed to be 99% by HPLC. After cooling to 25° C., the insoluble materials are separated by filtration to give 3-cyano-4-hydroxybenzoic acid (4-morpholinyl)amide. The yield is 453 mg (97.6%) when determined by HPLC.

EXAMPLE 27

3-Cyano-4-hydroxybenzoic acid (4-morpholinyl)amide (10 g, 43.1 mmol), sodium iodide (3.2 g, 21.3 mmol), potassium carbonate (17.9 g, 129 mmol) and tetramethylammonium chloride (0.47 g, 4.29 mmol) are suspended in acetone (125 mL) and water (15 mL), and the mixture is refluxed for 1 hour. After cooling to 30° C., chloroacetic acid (8.1 g, 86.2 mmol) is added. The mixture is refluxed for 5 hours, cooled to 30° C., and thereto are added potassium carbonate (11.9 g, 86.2 mmol) and chloroacetic acid (8.1 g, 86.2 mmol) successively. The mixture is refluxed for 3 hours, cooled to 30° C., and thereto are added potassium carbonate (11.9 g, 86.2 mmol) and chloroacetic acid (8.1 g, 86.2 mmol) successively. The mixture is refluxed for 3 hours, and thereto is added water (140 mL, 14 V), followed by addition of conc. hydrochloric acid (35 mL, 0.40 mol) at 40° C. or below. The mixture is stirred at 20° C. for one hour. The precipitated crystals are collected by filtration, and dried with a conical dryer to give 3-cyano-4-carboxymethoxybenzoic acid (4-morpholinyl)amide (11.6 g, 93.0%, content: 96.6%). Mp: 205-206° C.

EXAMPLE 28

3-Cyano-4-carboxymethoxybenzoic acid (4-morpholinyl)amide (10 g, 0.0345 mol) is suspended in dichloromethane (50 ml), and thereto is added N-methylmorpholine (3.79 ml, 0.0345 mol) for dissolution. After adding thionyl chloride (2.8 ml, 0.0396 mol) under ice-cooling, the mixture is stirred at room temperature overnight. A solution of 2-amino-5-chloropyridine (4.87 g, 0.0379 mol) and pyridine (6.10 ml, 0.0758 mol) in methylene chloride (150 ml) is ice-cooled, and thereto is added dropwise the previously prepared acid chloride solution. After stirring at room temperature for 30 minutes, the reaction solution is washed with 10% hydrochloric acid, water, aqueous saturated sodium bicarbonate, and water, successively, dried over magnesium sulfate, and evaporated to remove the solvent to give 3-cyano-4-(5-chloropyridin-2-ylaminocarbonylmethoxy)benzoic acid (4-morpholinyl)amide (13.3 g, 96%).

EXAMPLE 29

3-Cyano-4-carboxymethoxybenzoic acid (4-morpholinyl)amide (10 g, 34.5 mmol) is suspended in dichloromethane (50 mL, 5 V), and thereto are added thionyl chloride (5 mL, 8.2 g, 68.5 mmol) and dimethylformamide (0.13 mL, 126 mg, 1.72 mmol) successively at room temperature. The reaction solution is stirred under the reflux condition for 2 hours to give acid chloride. The acid chloride is added to a solution of 2-amino-5-chloropyridine (8.8 g, 68.5 mmol) and pyridine (11.1 mL, 10.9 g, 0.14 mol) in dichloromethane (150 mL) at 15° C. or below under ice-cooling over 6 hours. After confirming the completion of the reaction (about 5 minutes) by HPLC, the reaction solution is washed with 10% hydrochloric acid, water, 5% aqueous sodium hydrogen carbonate solution, and water (50 mL each) in this order, and dried over magnesium sulfate. The resulting filtrate is concentrated under reduced pressure in a bath at external temperature of 40-50° C. The residue is concentrated after adding tetrahydrofuran (50 mL) to give residue of 3-cyano-4-(5-chloropyridin-2-ylaminocarbonylmethoxy)benzoic acid (4-morpholinyl)amide.

The resulting concentration residue of 3-cyano-4-(5-chloropyridin-2-ylaminocarbonylmethoxy)benzoic acid (4-morpholinyl)amide is suspended in tetrahydrofuran (70 mL, 5V/W), and thereto is added 1,8-diazabicyclo[5.4.0]undec-7-en (5.7 mL, 6.3 g, 41.4 mmol), and the mixture is heated at 70° C. for about 4 hours. The mixture is then cooled to 35° C., and thereto is added dropwise water (210 mL, 15 V/W) over 1.5 hours, followed by stirring at room temperature for another 30 minutes. The precipitated crystals are collected by filtration, washed with a mixed solvent of water and tetrahydrofuran ($H_2O$/THF=3/1, 70 mL, 5 V/W), and dried at 50° C. under reduced pressure to give 3-amino-5-(morpholinyl-4-ylcarbonyl)-N-(5-chloropyridin-2-yl)benzofuran-2-carboxamide (10.0 g, yield: 72.1%, purity: 100%, corrected yield: 76%).

IR: ν=3306, 1655, 1629, 1572, 1522, 1452, 1378 $cm^{-1}$
MS: m/z=401[(M+1)$^+$]

EXAMPLE 30

3-Cyano-4-hydroxybenzoic acid (4-morpholinyl)amide (10 g, 43.1 mmol) and potassium carbonate (6.55 g, 47.3 mmol) are suspended in dimethylformamide (30 mL), and thereto is added methyl bromoacetate (4.28 mL, 45.3 mmol) at room temperature. After reacting at 50° C. for one hour, 1,8-diazabicyclo[5.4.0]undec-7-ene (6.54 g, 43.1 mmol) is added and warmed to 70° C. The mixture is stirred overnight, and partitioned by adding 10% hydrochloric acid (33 mL), water (150 mL) and ethyl acetate (150 mL). The aqueous layer is re-extracted with ethyl acetate (100 mL) (×2), and adjusted to pH 5 with sodium bicarbonate, followed by re-extraction of aqueous layer with ethyl acetate (100 mL) (×5) The organic layers are combined, and washed with a mixture of aqueous sodium bicarbonate and brine. The aqueous layer is re-extracted with ethyl acetate (100 mL) (×2). The organic layers are combined, dried over magnesium sulfate, and concentrated. To the residue are added ethyl acetate (10 mL) and hexane (30 mL). The precipitated crystals are collected by filtration, and dried with a conical dryer to give methyl 3-amino-5-(morpholinyl-4-ylcarbonyl)-benzofuran-2-carboxylate (9.74 g, 74.2%).

IR: ν=1702, 1638, 1607 $cm^{-1}$
MS: m/z=218 [(M+1)$^+$]

EXAMPLE 31 trans-4-(2-Pyrrolidon-1-yl)cyclohexylcarboxylic acid (7.9 g, 0.037 mol) is suspended in methylene chloride (50 mL, 5 V/W) in a four-necked flask (300 mL) under ice-cooling. Thionyl chloride (4.9 g, 0.041 mol) is added dropwise to the suspension, and the mixture is stirred at 10-20° C. for 30 minutes. After confirming the disappearance of the starting material, the reaction solution is evaporated under reduced pressure to give an acid chloride of trans-4-(2-pyrrolidon-1-yl)cyclohexylcarboxylic acid. Separately, 3-amino-5-(morpholinyl-4-ylcarbonyl)-N-(5-chloropyridin-2-yl)benzofuran-2-carboxamide (10 g, 0.025 mol) is suspended in methylene chloride (50 mL, 5 V/W) and pyridine (9.9 g, 0.125 mol), and thereto is added dropwise a suspension of an acid chloride of trans-4-(2-pyrrolidon-1-yl)cyclohexylcarboxylic acid in methylene chloride (50 mL, 5 V/W) at 10° C. or below. The mixture is stirred at the same temperature for 25 minutes, when the completion of the reaction is confirmed. The reaction solution is then partitioned by adding water (50 mL, 5 V/W). The organic layer is washed with 10% hydrochloric acid (100 mL, 10 V/W) and filtered, and the filtrate is concentrated. The resulting concentration residue is concentrated after adding ethanol (10 ml, 1V/W). To the resulting concentration residue are then added ethanol (96 mL, 9.6 V/W) and purified water (24 mL, 2.4 V/W), and the mixture is heated to reflux until it is confirmed that the residue completely dissolved. To the solution is added purified water (72 mL, 7.2 V/W) at 65° C. or above, and seeded with trans-5-(morpholin-4-ylcarbonyl)-3-[4-(2-oxo-pyrrolidin-1-yl)cyclohexylcarbonylamino]-N-(5-chloropyridin-2-yl)benzofuran-2-carboxamide hydrate. After confirming the precipitation of crystals, the solution is cooled to 30° C. over 2 hours, and the crystallizing solution is further cooled to a temperature of 10° C. or below. The precipitated crystals are collected by flirtation and washed with purified water until the pH of filtrate becomes 7. The resulting crystals are air-dried at 40° C. to give trans-5-(morpholin-4-ylcarbonyl)-3-[4-(2-oxo-pyrrolidin-1-yl)cyclohexylcarbonylamino]-N-(5-chloropyridin-2-yl)benzofuran-2-carboxamide hydrate (14.7 g, yield: 96.4%, theoretical value: 15.27 g (calculated as a hydrate)).

IR: ν=3266, 1707, 1635, 1527, 1492, 1462 $cm^{-1}$

Wet crystals obtained by filtering the crystallizing solution are dried at 80° C. under reduced pressure to give trans-5-(morpholin-4-ylcarbonyl)-3-[4-(2-oxo-pyrrolidin-1-yl)cyclohexylcarbonylamino]-N-(5-chloropyridin-2-yl)benzofuran-2-carboxamide (type I anhydride).

IR: ν=2857, 1703, 1670, 1644, 1577, 1541 $cm^{-1}$
MS: m/z=594 [(M+1)$^+$]
Mp: 253-255° C.

EXAMPLES 32-42

The corresponding bromides are treated in a similar manner to Example 26 to give the compounds as listed in the following Table.

| Example No. | product | method yield | physical properties, etc. |
|---|---|---|---|
| 32 | (acetyl-benzonitrile structure) | A 82% | powder MS: m/z = 145[M$^+$] |
| 33 | (dicyanopyridine structure) | A 63% | powder MS: m/z = 105[(M + 1)$^+$] |
| 34 | NC—⟨benzene⟩—NH$_2$ | B 65% | powder MS: m/z = 119[(M + 1)$^+$] |

-continued

| Example No. | product | method yield | physical properties, etc. |
|---|---|---|---|
| 35 | HO—⌬—NC (2-hydroxybenzonitrile) | B 60% | powder MS: m/z = 119[M⁺] |
| 36 | binaphthyl-2,2'-dicarbonitrile | C 98% | powder MS: m/z = 305[(M + 1)⁺] |
| 37 | 1-naphthonitrile | D 92% | powder MS: m/z = 153[M⁺] |
| 38 | NC—⌬—CF₃ | A 94% | powder MS: m/z = 171[M⁺] |
| 39 | NC—⌬—CO₂Me | A 97% | powder MS: m/z = 161[M⁺] |
| 40 | NC—⌬—OMe | D 89% | powder MS: m/z = 133[M⁺] |
| 41 | 2-(dimethylamino)benzonitrile | D 93% | oil MS: m/z = 145[M⁺] |
| 42 | benzothiophene-3-carbonitrile | D 89% | powder MS: m/z = 159[M⁺] |

Method A: Br₂ (0.2 equiv.), Zn(CN)₂ (0.6 equiv.), Pd/C (4 mol %), PPh₃ (0.16 equiv.), Zn (0.4 equiv.), 80° C., 4-5 hours
Method B: Br₂ (0.4 equiv.), Zn(CN)₂ (0.5 equiv.), Pd/C (8 mol %), PPh₃ (0.32 equiv.), Zn (1.2 equiv.), 125° C., 4 hours
Method C: Br₂ (0.4 equiv.), Zn(CN)₂ (1.0 equiv.), Pd/C (8 mol %), dppf (0.32 equiv.), Zn (0.8 equiv.), 120° C., 15 hours
Method D: Br₂ (0.2 equiv.), Zn(CN)₂ (0.6 equiv.), Pd/C (4 mol %), PPh₃ (0.16 equiv.), Zn (0.4 equiv.), 115° C., 2-8 hours

INDUSTRIAL APPLICABILITY

The present invention makes it possible to produce efficiently a benzofuran derivative or a pyridofuran derivative useful as a medicament or a pharmaceutically acceptable salt thereof, which is useful as an inhibitor of activated blood coagulation factor X.

The invention claimed is:

1. A process for preparing a compound of the formula [1]:

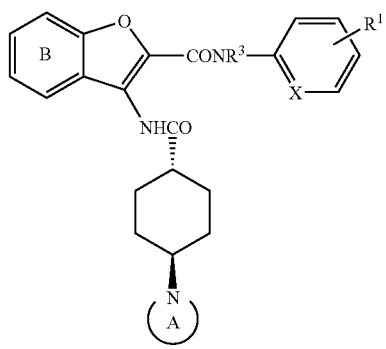

wherein X is a group of the formula: —N= or —CH=; $R^1$ is a hydrogen atom, a halogen atom, a lower alkyl group, a lower alkoxy group, a cyano group or an amino group optionally substituted by a lower alkyl group; Ring A is a nitrogen-containing heterocyclic group; Ring B is an optionally substituted benzene ring or an optionally substituted pyridine ring; and $R^3$ is a hydrogen atom or a lower alkyl group, or a pharmaceutically acceptable salt thereof, which comprises:

(A)
1)-a) reacting a compound of the formula [II]:

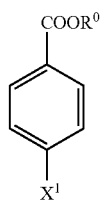

wherein $R^0$ is a hydrogen atom or a lower alkyl group and $X^1$ is a leaving group with a compound of the formula [III]:

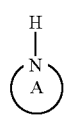

wherein Ring A is a nitrogen-containing heterocyclic group, or

1)-b) reacting a compound of the formula [IV]:

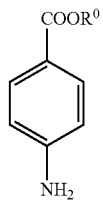

wherein the symbol is the same a defined above with a compound of the formula [V]:

wherein A' is a group derived from a nitrogen-containing heterocyclic group with a nitrogen atom, removed, and $X^2$ and $X^3$ are leaving groups;

2) subjecting the resulting compound of the formula [VI]:

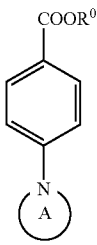

wherein the symbols are the same as defined above to catalytic reduction;

3) subjecting the resulting the compound of the formula [VII]:

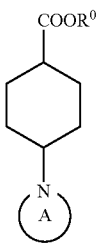

wherein the symbols are the same as defined above to lower-alkyl esterification when $COOR^0$ is a carboxyl group, followed by isomerization to give a trans-form compound of the formula [VIII]:

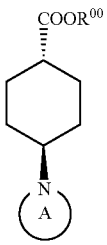

wherein $R^{00}$ is a hydrogen atom or a lower alkyl group and the other symbol is the same as defined above; and separately, (B)
1) cyanation of a compound of the formula [IX]:

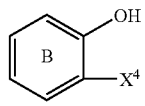

wherein Ring B is an optionally substituted benzene ring or an optionally substituted pyridine ring and $X^4$ is a leaving group, 2) reacting the resulting compound of the formula [X]:

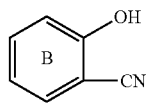

wherein the symbol is the same as defined above with a compound of the formula [XI]:

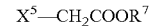

wherein $R^7$ is a hydrogen atom or a lower alkyl residue selected from a group consisting of methyl residue and ethyl residue and $X^5$ is a leaving group, converting said lower alkyl residue to a hydrogen atom when $R^7$ is a lower alkyl residue, and reacting the resulting compound of the formula [XII]:

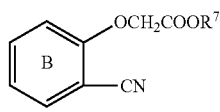

wherein the symbols are the same as defined above with a compound of the formula [XIII]:

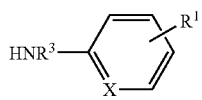

wherein $R^3$ is a hydrogen atom or a lower alkyl group, $R^1$ is a hydrogen atom, a halogen atom, a lower alkyl group, a lower alkoxy group, a cyano group or an amino group optionally substituted by a lower alkyl group and X is a formula: —N= or —CH=, 3) cyclizing the resulting compound of the formula [XIV]:

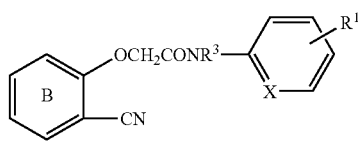

wherein the symbols are the same as defined above to give a compound of the formula [XV]:

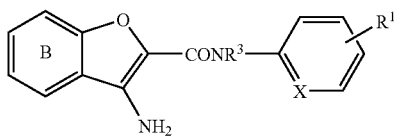

wherein the symbols are the same as defined above; and
(C)
reacting a compound of the formula [XV] with a compound of the formula [VIII] or an acid halide thereof; and
wherein each of the leaving groups of $X^1$-$X^5$ includes a halogen atom and sulfonic acid ester residues selected from the group consisting of an arylsulfonyloxy group, a lower-alkylsulfonyloxy group and a perhalogenolower-alkylsulfonyloxy group.

2. The process according to claim 1, wherein the reaction between the compound of the formula [II] and the compound of the formula [III] is carried out under nitrogen in the presence of a catalyst, a ligand and a base in an inert solvent.

3. The process according to claim 2, wherein the catalyst includes homogeneous and heterogeneous catalysts.

4. The process according to claim 3, wherein the homogenous catalyst includes palladium acetate and the heterogeneous catalyst includes a group VIII metal compound supported by a solid phase.

5. The process according to claim 2, wherein the ligand includes diphenylphosphino compounds selected from the group of consisting of 2.2'-bis(diphenylphosphino)-1,1'-binaphthyl and 1,1'-bis(diphenylphosphino)ferrocene, triphenylphosphines.

6. The process according to claim 2, wherein the base includes an inorganic base and an organic base.

7. The process according to claim 2, wherein the palladium catalyst is used in an amount of approximately 0.001-0.1 equivalent, the ligand is used in an amount of approximately 0.002-0.2 equivalent, and the base is used in an amount of approximately 1-2 equivalent in relation to the compound of the formula [II].

8. The process according to claim 2, wherein the reaction is carried out at 0° C.-200° C.

9. The process according to claim 1, wherein the reaction between the compound of the formula [IV] and the compound of the formula [V] is carried out in the presence of a base in an inert solvent.

10. The process according to claim 9, wherein the base is used in an amount of approximately 2-10 equivalent in relation to the compound of the formula [IV].

11. The process according to claim 9, wherein the reaction is carried out at 0° C.-30° C.

12. The process according to claim 1, wherein the catalytic reduction of the compound of the formula [VI] is carried out in the presence of a catalyst under hydrogen pressure in an inert solvent.

13. The process according to claim 12, wherein the hydrogen pressure ranges from 7 to 30 atm.

14. The process according to claim 12, wherein the catalyst includes a rhodium-carbon, and is used in an amount of approximately 0.01-0.1 equivalent in relation to the compound of the formula [VI].

15. The process according to claim 12, wherein the reaction is carried out at −20 C.-120° C.

16. The process according to claim 1, wherein the catalytic is carried out under a condition of pH 7-8.

17. The process according to claim 1, wherein the lower-alkyl esterification of the compound of the formula [VII] is carried out by treating the compound with a lower alkanol in an acid condition in an inert solvent.

18. The process according to claim 1, wherein the isomerization of the compound [VII] is carried out in the presence of a base in an appropriate solvent.

19. The process according to claim 18, wherein the base includes alkali metal alkoxides and alkali metal amides, and the solvent includes an inert solvent.

20. The process according to claim 19, wherein the base is used in an amount of approximately 1-2 equivalent in relation to the compound of the formula [VII].

21. The process according to claim 18, wherein the isomerization reaction is carried out at −20° C.-150° C.

22. The process according to claim 1, wherein the cyanation of the compound of the formula [IX] is carried out by treating the compound with a cyanizing agent in the presence of a catalyst, zinc and a ligand.

23. The process according to claim 22, wherein the cyanizing agent includes zinc cyanide, copper cyanide, potassium cyanide, sodium cyanide, and acetone cyanohydrin.

24. The process according to claim 1, wherein the reaction between the compound of the formula [X] and the compound of the formula [XI] is carried out in the presence of a halogenating agent and a base in an inert solvent.

25. The process according to claim 24, wherein the reaction is carried out at 0° C.-60° C.

26. The process according to claim 1, wherein the reaction between the compound of the formula [XII] and the compound of the formula [XIII] is carried out in the presence of a halogenating agent and a base in an inert solvent.

27. The process according to claim 1, wherein the cyclization of the compound of the formula [XIV] is carried out in the presence of a base in an inert solvent.

28. The process according to claim 27, wherein the base is used in an amount of approximately 0.05-2.2 equivalent in relation to the compound of the formula [XIV].

29. The process according to claim 27, wherein the reaction is carried out at 0° C.-100° C.

30. The process according to claim 1, wherein the reaction between the compound of the formula [XV] and the compound of the formula [VIII] or an acid halide thereof is carried out in the presence of a base in an inert solvent.

31. The process according to claim 30, wherein the reaction is carried out at 15° C.-25° C.

* * * * *